United States Patent
Wilssens

(10) Patent No.: US 8,382,684 B2
(45) Date of Patent: Feb. 26, 2013

(54) METHOD AND APPARATUS FOR DISPLAYING 3D IMAGES OF A PART OF THE SKELETON

(75) Inventor: Jean-Pierre Wilssens, Beveren (BE)

(73) Assignee: RSSCAN International, Olen (BE)

( * ) Notice: Subject to any disclaimer, the term of this patent is extended or adjusted under 35 U.S.C. 154(b) by 971 days.

(21) Appl. No.: 11/886,127

(22) PCT Filed: Mar. 10, 2006

(86) PCT No.: PCT/EP2006/002214
§ 371 (c)(1),
(2), (4) Date: Apr. 24, 2008

(87) PCT Pub. No.: WO2006/094817
PCT Pub. Date: Sep. 14, 2006

(65) Prior Publication Data
US 2009/0163834 A1    Jun. 25, 2009

Related U.S. Application Data

(60) Provisional application No. 60/660,468, filed on Mar. 11, 2005.

(30) Foreign Application Priority Data

Mar. 11, 2005  (GB) .................................. 0505038.0

(51) Int. Cl.
*A61B 5/103* (2006.01)
(52) U.S. Cl. ......................................... 600/592; 33/515
(58) Field of Classification Search .................. 600/592; 33/515
See application file for complete search history.

(56) References Cited

U.S. PATENT DOCUMENTS

| 4,267,728 A | 5/1981 | Manley et al. |
| 4,813,436 A | 3/1989 | Au |

FOREIGN PATENT DOCUMENTS

WO    WO 95/31933    11/1995

OTHER PUBLICATIONS

Gefen "Biomechanical analysis of fatigue-related foot injury mechanisms in athletes and recruits during intensive marching" IFMBE 2002. 302-310.*
Gefen et al. "Biomechanical analysis of the three-dimensional foot structure during gait: a basic tool for clinical applications" ASME 2000, 630-639.*
Han et al. "Quantification of hte path of center of pressure (COP) using an F-scan in-shoe transducer" Elsevier Gait and Posture 1999, 248-254.*
Chao "Graphic-based musculoskeletal model for biomechanical analyses and animation" Medical Engineering and Physics 2003. p. 201-212.*
Shuizong Hong et al., "New Type of Human Plantar Static and Dynamic Pressure Test System", *Shanghai J. of Biomedical Engineering*, Mar. 3, 1985. (ISSN 1006-1517.0 Mar. 6, 1985).
Office Action of PRC regarding Chinese Patent Application No. 200680012474.1, Apr. 24, 2009.

(Continued)

*Primary Examiner* — Max Hindenburg
*Assistant Examiner* — Renee Danega
(74) *Attorney, Agent, or Firm* — Bacon & Thomas, PLLC

(57) ABSTRACT

The present invention relates to a method of displaying pressures and forces on a part of the skeleton such as the feet which relate to movements of the human or animal body, especially movements of the lower skeleton, e.g. foot, ankle, knee or hip; as well as to a method of displaying these movements based on the measured pressures and forces on the feet. The present invention also includes apparatus for displaying these pressures and forces and/or movements and software for use in the apparatus. In particular eversion or inversion motion of the foot is displayed.

17 Claims, 19 Drawing Sheets

OTHER PUBLICATIONS

Gefen A. et al., Biochemical analysis of the three-dimensional foot structure during gait: a basic tool for clinical applications, Journal of Biochemical Engineering, vol. 122, No. 6, Dec. 2000, pp. 630-639 (XP008066848).

Hastings M K et al., "Aligning anatomical structure from spinal X-ray computed tomography with plantar pressure data", Clinical Biomechanics, Butterworth Scientific Ltd.. Guildford, GB, vol. 18, No. 9, Nov. 2003, pp. 877-882 (XP004460221).

* cited by examiner

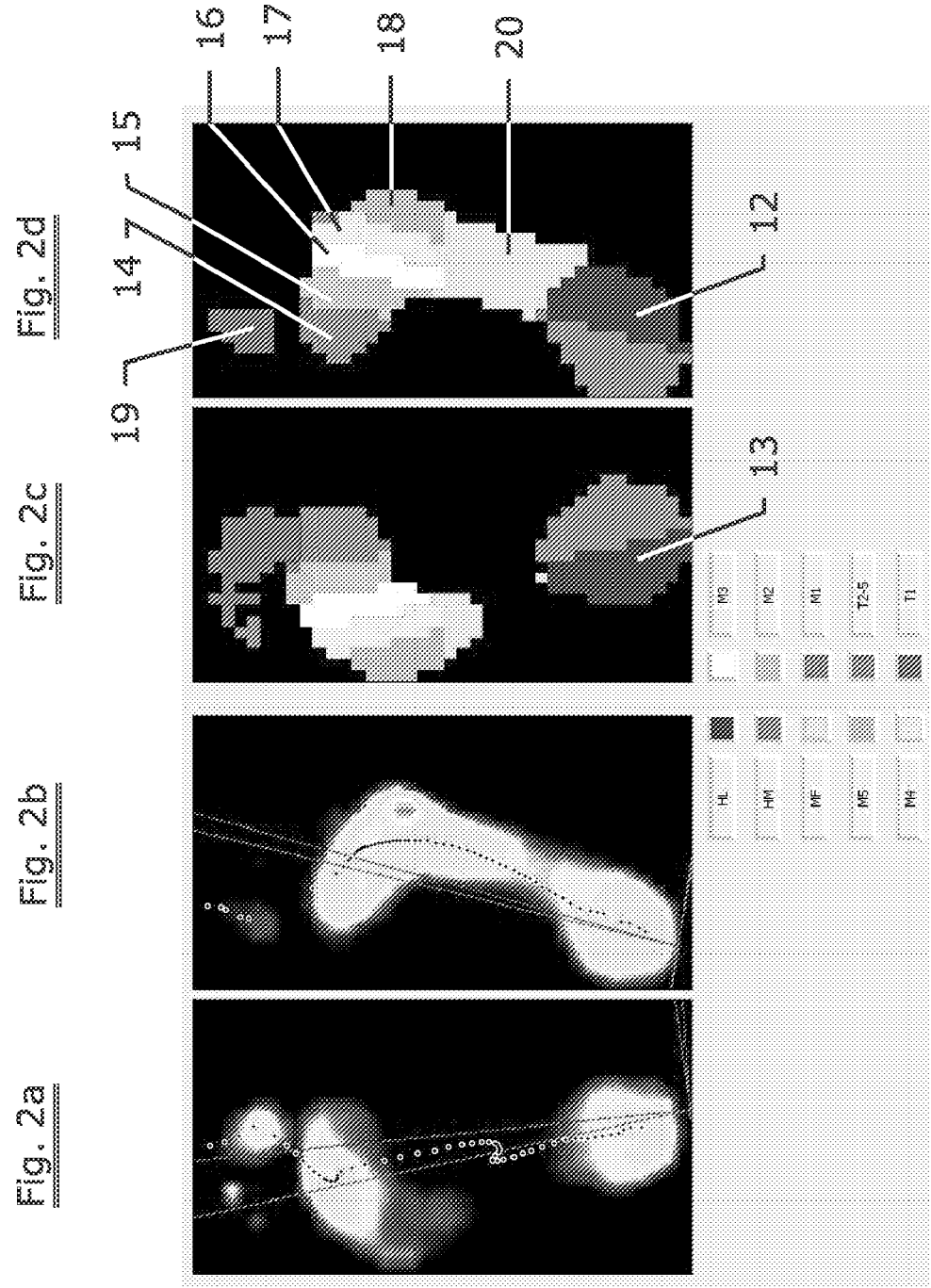

METHOD AND APPARATUS FOR DISPLAYING 3D IMAGES OF A PART OF THE SKELETON

FIELD OF THE INVENTION

The present invention relates to a method of displaying pressures and forces on a part of the skeleton such as the feet which relate to movements of the human or animal body, especially movements of the lower skeleton, e.g. foot, ankle, knee or hip; as well as to a method of displaying these movements based on the measured pressures and forces on the feet. The present invention also includes apparatus for displaying these pressures and forces and/or movements and software for use in the apparatus. In particular eversion or inversion motion of the foot is displayed.

BACKGROUND INFORMATION

Repetitive movements such as jogging or running training can induce injuries. Running injuries have been analysed and reported by Knutsen and Hart in chapter 22 of "Epidemiology of Sports Injuries", ed. D. Caine et al., Human Kinetics, 1996. There is some consensus that injuries develop gradually, i.e. a cumulative effect of repetitive loading, however severe training sessions may also exacerbate an injury. A common injury is knee pain, however injuries of tendons such as the Achilles tendon or posterior tibial tendonitis, plantar fasciitis, pes planovalgum, metatarsalgia and calcaneal spurs, adductor strain, iliofibial band friction syndrome, iliotibial strain, tibial stress syndrome, patello-femoral pain, ankle sprain, back pain especially lower back pain and sciatica, hip or groin pain, thigh pain, foot sprain, and bursitis, have also been reported.

To alleviate these effects it has been proposed to correct training errors, correct muscle imbalance, identify and correct structural abnormalities, correct running style, use running shoes, identify injury early, treat the injury early, prescribe and use orthotics, etc. To achieve these a physical examination of the person is recommended including an identification and assessment of kinetic chain dysfunction as well as identification of previous injuries and measurement of anthropometric and functional characteristics associated with risk of running injury.

A wide variety of diagnostic methods are available to the doctor, e.g. CT-scan, X-ray, MRI scan as well as physical examination. However these are usually carried out in a static mode. There remains a need for a method of identifying potential injuries as well as to diagnose the cause of existing injuries which is easy to use, requires equipment which need not be in a clinic or hospital and which need not be operated by trained medical staff.

U.S. Pat. No. 4,267,728 discloses an apparatus for analysing the foot comprising television cameras for photographing the gait of the subject and for photographing the plantar surface of the foot through a transparent platform. The platform comprises beams each of which is supported at each end by means for detecting load imposed on each beam. The apparatus also includes circuitry for determining the centre of pressure applied to each beam. The centres of pressure and the video outputs from the cameras are displayed on a suitable display.

A further apparatus is known from WO 95/31933 using a walking belt. During a constant walking phase pressure sensors are used to determine the dynamic pressure effect of the feet together with the change in relative position of selected parts of the body by two-dimensional angle measurements and a muscle potential measurement. Also the gait is monitored by video cameras.

U.S. Pat. No. 4,813,436 describes another system for motion analysis comprising markers secured at various joints as well as pressure sensitive shoes or insoles. The subject is photographed during motion using two video carriers. The gait, the angular position of the various joints and other information indicative of walking characteristics are displayed.

These known methods require the use of cameras with each patient to be examined which is complex and expensive. An additional problem with cameras and complex equipment is that it tends to distract the patient and movements may be carried out in an abnormal manner. Hence there is a need to provide equipment for analysing gait which is simple and unobtrusive. Still a further problem is that interpretation of the copious and complex data is difficult even for trained doctors and orthopaedic specialists.

SUMMARY OF THE INVENTION

An object of the present invention is to provide a method and apparatus to assist in diagnosis of problems of body posture or movement especially of stance and gait defects or problems, as well as to assist in the diagnosis of strains caused by repetitive movement during training. The present invention provides methods for displaying pressures and forces on the feet and relating these to movements of parts of the human or animal body, especially movements of the lower skeleton, e.g. foot, ankle, knee or hip; as well as to a method of displaying at least some of these movements based on the measured pressures and forces on the feet.

A further object of the present invention is to provide apparatus for displaying these pressures and forces and/or movements and software for use in the apparatus. In particular means are provided for display of eversion or inversion motion of the foot. An advantage of the apparatus and methods of the present invention is that they do not require the use of a video camera for every human or animal to be examined but only for capturing initial values.

In one aspect, the present invention provides a method of displaying pressure distributions on the foot of a human or animal during motion using a pressure sensing device, the method comprising: capturing from the pressure sensing device pressures exerted by the foot during standing or motion and deriving therefrom pressure for at least three segments of the impacting foot surface; and deriving time evolutions of the pressure values for at least three segments of the impacting surface of the foot. The method further includes displaying the time evolutions of the pressure values of the at least three segments of the impacting surface of the foot. In addition the time evolutions of combinations of at least two pressure values from two different segments of the impacting foot surface may be calculated and displayed. The display of any pressure values may be combined with a display of reference values for the same parameter, e.g. as obtained from a representative number of healthy persons of the population.

The present invention also provides a method of displaying a 3D representation of bones of the foot and bones attached thereto of a human or animal either when stationary or during motion using a pressure sensing device, the method comprising: capturing from the pressure sensing device pressures exerted by the foot during standing or motion and deriving therefrom pressure values for segments of the impacting foot surface; deriving from the captured pressure values, changes in position of one or more of the bones; and displaying a 3D image of the foot and attached bones including the changes in position of the one or more bones.

The method may comprise the step of deriving from the captured pressure values a degree of pronation or supination of at least heel and the forefoot segments. These are useful parameters as they are related to bone movements, e.g. tibia rotation. The degree of pronation or supination of each of at least the heel segment and the forefoot segment can be displayed as a function of a time in separate displays. The use of separate displays makes comparisons easier.

The method can also comprise capturing from the pressure sensing device pressures on the foot when stationary or during motion and deriving therefrom a degree of pronation or supination of at least the heel and the midfoot and forefoot. These can be displayed for at least the heel and the midfoot the forefoot as a function of a time in separate displays. The method preferably includes displaying the degree of pronation or supination as a function of the time elapsed between contact by the heel and lift-off of the forefoot.

To aid in identifying abnormal features the method may include displaying a reference degree of pronation or supination of at least the heel and the forefoot at the same time as displaying the degree of pronation or supination of at least the heel and the forefoot of the human or animal, for example displaying a reference degree of pronation or supination of at least the heel and the midfoot and forefoot at the same time as displaying the degree of pronation or supination of at least the heel, the midfoot and the forefoot of the human or animal.

The present invention also provides an apparatus for displaying a 3D representation of bones of the foot and bones attached thereto of a human or animal either when stationary or during motion using a pressure sensing device, comprising: means for capturing from the pressure sensing device pressures on the foot during standing or motion and deriving; means for deriving from the captured pressures, changes in position of one or more of the bones; and means for displaying a 3D image of the foot and attached bones including the changes in position of the one or more bones.

The apparatus may comprise means for deriving from the captured pressures a degree of pronation or supination of at least the heel and the forefoot. The apparatus may comprise means for displaying the degree of pronation or supination of each of at least the heel and the forefoot as a function of a time in separate displays.

The apparatus may comprise means for deriving from the pressures measured by the pressure sensing device a degree of pronation or supination of at least the heel and the midfoot and forefoot and means for displaying the degree of pronation or supination of each of at least the heel and the midfoot the forefoot as a function of a time in separate displays. For example, the apparatus has means for displaying the degree of pronation or supination as a function of the time elapsed between contact by the heel and lift-off of the forefoot. The apparatus may further comprise means for displaying a reference degree of pronation or supination of at least the heel and the forefoot at the same time as displaying the degree of pronation or supination of at least the heel and the forefoot of the human or animal. In addition the apparatus may comprise means for displaying a reference degree of pronation or supination of at least the heel and the midfoot and forefoot at the same time as displaying the degree of pronation or supination of at least the heel, the midfoot and the forefoot of the human or animal.

The present invention also includes a computer program product comprising code, which when executed on a processing engine, carries out any of the methods of the present invention. The present invention also includes a machine readable storage device storing the computer program product.

BRIEF DESCRIPTION OF THE DRAWINGS

The present invention will now be described by way of example only and with reference to the accompanying drawings, in which:

FIGS. 2A to D show in 2A and B the pressure distributions on left and right feet, and in 2C and D a segmentation of these pressure distributions into a finite number of pressure zones.

FIG. 7 shows a neutral position (left foot), FIG. 8 shows rearfoot supination (left foot), FIGS. 9 and 10 show rearfoot pronation (left foot).

FIG. 15 shows midfoot pronation (left foot), FIG. 16 shows midfoot pronation (left foot).

FIG. 18 shows forefoot supination and FIG. 19 shows forefoot pronation (left foot).

FIG. 22 shows flexible first ray (left foot).

FIG. 23 shows an unstable forefoot (left foot).

FIG. 25 shows an stable forefoot (left foot).

DESCRIPTION OF THE ILLUSTRATIVE EMBODIMENTS

Figure 1:
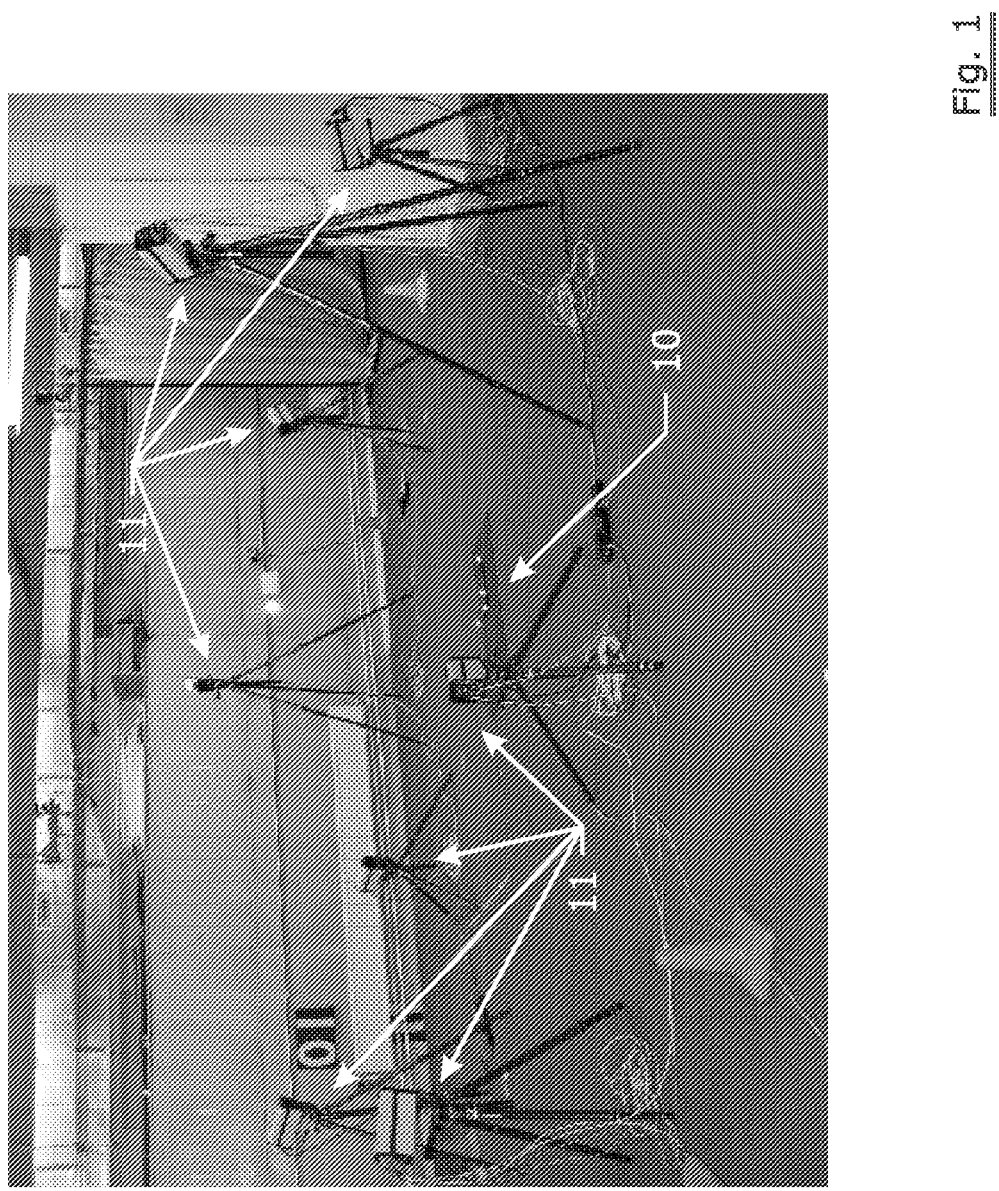
FIG. 1 shows schematically a set up for capturing initial values of pressure distributions exerted by the feet and one or more videos of the movement.

The present invention will be described with respect to certain embodiments and drawings but is not limited thereby or thereto but only by the claims.

The present invention relates to a method and apparatus for diagnosis of problems of body posture or movement especially of stance and gait defects or problems as well as for diagnosing strains caused by repetitive movement during training. For example, the present invention uses methods and apparatus for displaying pressures and forces on the feet and relating these to movements of the human or animal body, especially movements of the lower skeleton, e.g. foot, ankle, knee or hip. The present invention also provides a method of displaying at least some of these movements based on the measured pressures and forces on the feet and software for use in the apparatus. In particular means are provided for display of eversion or inversion motion of the foot. The methods of the present invention do not require the use of a video camera for every human or animal to be examined but only for capturing initial values.

The present invention provides means for the measurement of force and/or pressure distribution caused by the foot of a person or animal when stationary; i.e. standing, or when walking, hopping, jumping or running and the derivation from these measurements of information useful in the diagnosis or prevention or remediation of injury. In particular the information which is to be derived is movement of parts of the kinematic chain attached to the foot, especially rotation of the tibia, that is either external or internal rotation.

The present invention is based on the observation that although the limbs with their joints theoretically have a large number of degrees of freedom and a variety of movements, in fact these movements are limited when the person or animal is standing, running, hopping, jumping and walking by the need to keep the body in balance. Also the parts of the kinematic chain attached to the foot are not independent of each other. For instance when a human is standing upright and rotates the upper body, the pressure distribution of the feet changes caused by the internal linkages between the parts of the kinematic chain between the upper body and the foot. The present invention makes use of these dependencies to display motion of parts of the kinematic chain based only on pressure measurements carried out on the foot or feet.

In accordance with embodiments of the present invention the kinematics of parts of the lower limb such as the foot and also the ankle, tibia etc. are displayed in a 3D representation based on measurements of the temporal evolution of local pressures underneath the foot, e.g. during hopping, jumping, walking or running over a pressure measuring device. In one embodiment the kinematic modelling is provided by determining relationships empirically between the temporal evolution of the local pressures and the movement of the bones of the foot and the bones of the kinematic chain attached to the foot.

A first preliminary step in a method according to the present invention is to collect data as to pressure distributions exerted by the feet in certain activities such as standing, hopping, jumping, walking and ranging for a normal or average sample of the human or animal population. An arrangement to achieve this is shown in FIG. 1. It comprises a pressure sensing device 10 placed on the floor connected to suitable readout electronics and processing equipment with a visual display unit and a plurality of video and/or still cameras. The pressure sensing device 10 may be a pressure sensing array of sensors, e.g. the commercially available product type FootScan as supplied by RsScan, Belgium. However, the present invention is not limited to a static pressure plate. The pressure exerted by a body part such as a foot can be measured by pressure sensors, e.g. an array of pressure sensors which are placed in or integrated into the sole of a shoe. Using such a pressure sensor, the subject may stand, hop, jump, walk or run on a flat surface or on a moving band as disclosed in WO 95/31933.

The subject stands, hops, jumps, walks or runs on the pressure sensing device 10 and the local pressures of a foot or feet of the subject during standing or motion are captured while at the same time taking photographs and/or videos of the subject using one or more cameras 11.

Typical pressure plots are shown in FIG. 2. FIGS. 2a and 2b show the pressure distributions from left and right feet. The relative value of the pressure is shown as a variation in luminosity. It is preferred in accordance with an aspect of the present invention if this raw pressure data is simplified by segmenting the pressure plot into zones. These zones are preferably related to anatomically important zones of the foot. A particularly preferred segmentation is shown in FIGS. 2c and d. These zones are lateral heel (12), medial heel (13), metatarsals 1 to 5 and (14-18). Two zones, namely that of the largest toe (19) and the mid part (20) of the foot are preferably not used. The pressure distribution of the largest toe often has little bearing on the overall behaviour of the foot and the pressure distribution of the mid-port of the foot can be missing as in FIG. 2c or is always missing when a person wears shoes with a heel and a raised instep. As this pressure zone is not always present in a pressure plot it is preferred not to rely on it.

The lateral heel (12) and medial heel (13) pressure zones are self-explanatory. They indicate the pressure on each side of the heel. The pressure zones of the 5 metatarsals (14-18) relate to the pressure exerted by the 5 metatarsal bones.

For each of the above zones 12 to 18 a representative pressure is calculated. A suitable averaging scheme may be used to determine the average pressure, e.g. each zone can be broken up into smaller zones and the average for each of the smaller zones is averaged. Hence in this embodiment 7 pressures are recorded for the 7 zones ate each moment of time.

Figure 3A:
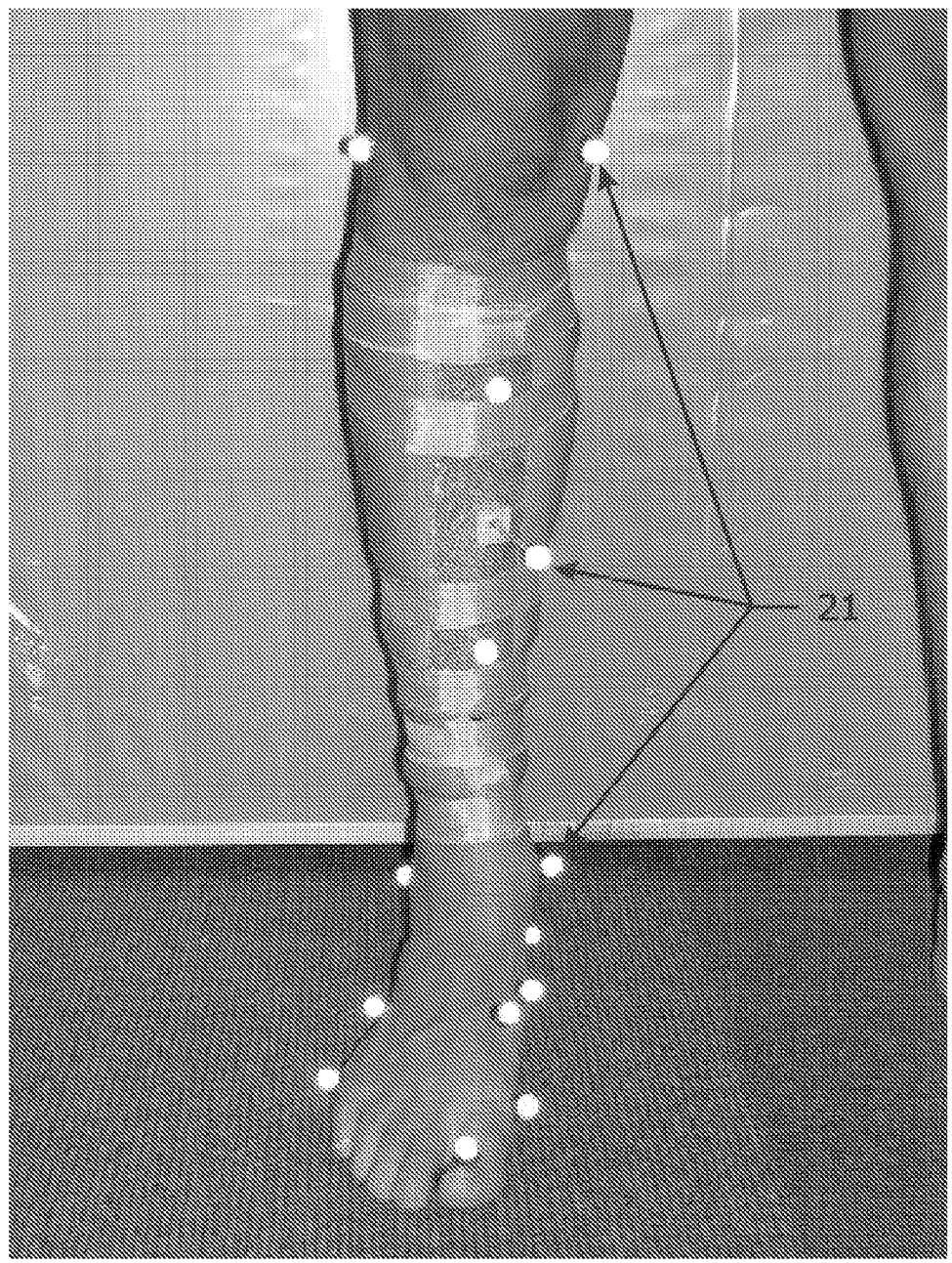
FIGS. 3A and B show in 3A the attachment of markers to the leg of an individual, and in 3B stills from a video of the movement of the legs and feet.

The subject who is to step onto the pressure plate preferably has markers 21 attached (see FIGS. 3a and b) to the leg and foot whose position and/or movement can be recorded by cameras 11. The markers 21 may be pins that penetrate through the skin and are attached to the bones of the subject. The protruding ends of the pins may have a suitable marker attached, such as a fluorescent marker as is known to the skilled person. To bring the markers to fluorescence, infra-red or ultra-violet lamps may be provided.

Figure 3B:
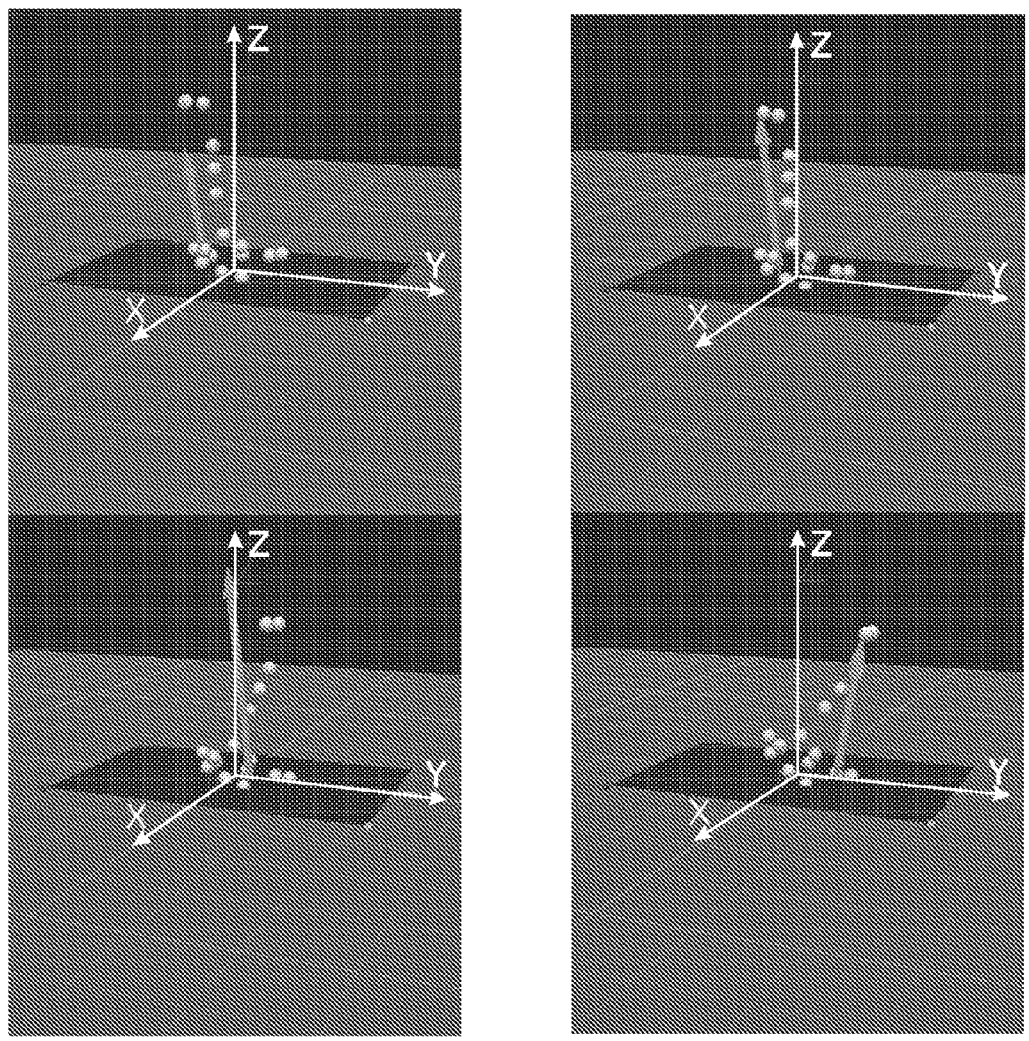

During each test run the pressure sensing device 10 is used to output and record the temporal evolution of the local forces and/or pressures on the foot during standing or motion. These pressures and forces can be stored in electronic form in mass storage, e.g. a magnetic disc memory such as a hard drive or a diskette, magnetic tape memory, optical discs such as CD-Rom or DVD-ROM. This stored values can then be converted into the seven pressure values for the seven pressure zones 12 to 18 either in real time or off-line. Similarly, the photographs and/or videos are captured by the cameras 11 are stored on similar mass storage (FIG. 3b). Preferably there is a common time base between all forms of recorded data so that each value in each recorded data can be compared with values in any other recorded data for the same subject. These data are stored as reference data for normal stance, gait running movement.

In accordance with an embodiment of the present invention the temporal evolution of the pressure values for the feet of normal subjects or other subjects to be diagnosed, e.g. during hopping, jumping, waling or running, is also displayed in a limited number of windows. Ideally these windows should be selected so that they have some anatomical relevance. During hopping, jumping, walking or running the heel generally strikes the ground first. For about the first 10% of the pressure/time plot the heel provides the major influence on the pressure distributions. As the body weight moves to directly above the foot, the heel and the metatarsal regions together (midfoot) are loaded. The body is in this midstance position for about a further 35 to 50%, i.e. between 45 and 60% of the pressure/time plot. Only the front of the foot (forefoot) is in contact with the ground at the moment of lift off, e.g. for the last 40% of the pressure/time plot. The local pressure records are preferably displayed and optionally stored in memory for at least the heel and the forefoot, and more preferably for the heel, midfoot and forefoot regimes of the pressure/time evolution. The values from the 7 pressure zones 12 and can be combined either by adding or subtracting to provide pressure values relating to particular anatomically important parameters of the gait. The heel pressure can be obtained by adding the lateral and medial heel pressure values from zones 12, 13 and normalising the result. Similarly, the forefont pressure can be obtained by adding the values from the 5 metatarsal zones 12 to 18 and normalising the result.

A preferred method of displaying the results is to record the pressure distribution and the centres of pressure of the foot, e.g. of any or all of the seven zones 12 to 18, such as the heel and forefoot and preferably the heel, midfoot and forefoot in terms of a degree of pronation or supination of at least the heel and the forefoot, and preferably the heel, mid foot and forefoot, preferably with time as the foot moves. The calculation of centre of pressure from such pressure measurements is well known to the skilled person, e.g. for each of the zones 12 to 18 as described above. The calculation of supination or pronation is done by comparing the pressure values of the seven zones on the left and right of the midline of the foot. Preferably the apparatus includes means for displaying the degree of pronation or supination of each of at least the heel and the forefoot, and preferably each of the heel, midfoot and forefoot as a function of a time in separate display screens. The degree of pronation or supination can be determined by analysing the relative pressures on either side of a midline of the foot, e.g. by subtracting the lateral heel value from the medial heel value.

Each display screen is preferably a static display which for instance shows the change in centre of pressures of the heel, midfoot and/or the forefoot with the X axis being time, e.g. displayed as a percentage of the time between first impact of the heel and lift-off of the toes, and the Y axis being the degree of supination or pronation. Such display screens show the balance of the parts of the foot, i.e. the degree of supination or pronation.

Figure 4:
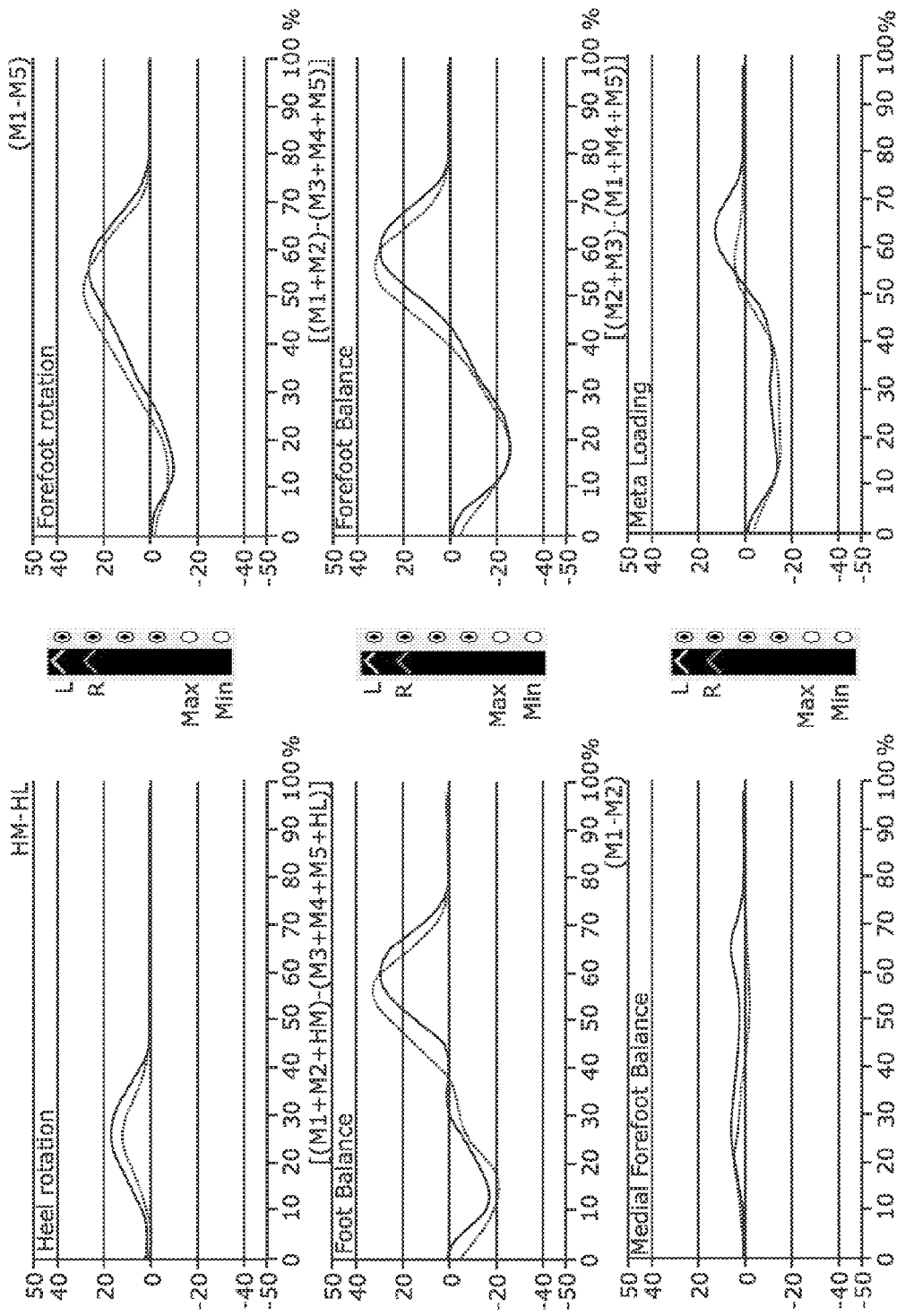
FIG. 4 shows 6 screens displaying the time evolution of various pressure measurements on feet in accordance with an embodiment of the present invention.

A set of suitable screen shots is shown in FIG. 4 in which pressure values are plotted in terms of percentage time between heel landing and toe lift-off. The screen shots are displays of the temporal change of at least one of:
1) heel rotation
2) foot balance
3) medial foot balance
4) forefoot balance
5) metatarsal loading.

A sixth screen showing forefont rotation can also be calculated and displayed. These screens will be described in more detail below.

By measuring these pressure values for a range of normal subjects a set of ideal curves of centre of pressure against time, e.g. plotted as a percentage of the time from first heel impact to lift-off of the toe are obtained based on normal subjects. One or more of the five displays for heel rotation, foot balance, medial foot balance, forefoot balance and/or metatarsal loading in terms of pronation/supination and time elapse can be obtained for normal subjects. There is always a spread of results so that these values are stored as normal ranges rather than isolated points. These normal ranges can be used as references when the pressure distributions of a subject to be examined are displayed.

An optional next preliminary step is to repeat the above experiments with persons with known gait disabilities. In this case display screens of abnormal behaviour for heel rotation, foot balance, medial foot balance, forefoot balance and/or metatarsal loading in terms of pronation/supination can be obtained and compared with the reference values.

The next preliminary step is to examine the photographs/video footage from the cameras 11 with the various display screens mentioned above and to determine the exact movement of the lower limb and absolute and relative motions of the bones as they relate to the pressure values. In determining the relationship between pressure distributions and bone movements, knowledge of the anatomy may be used.

Figure 12:
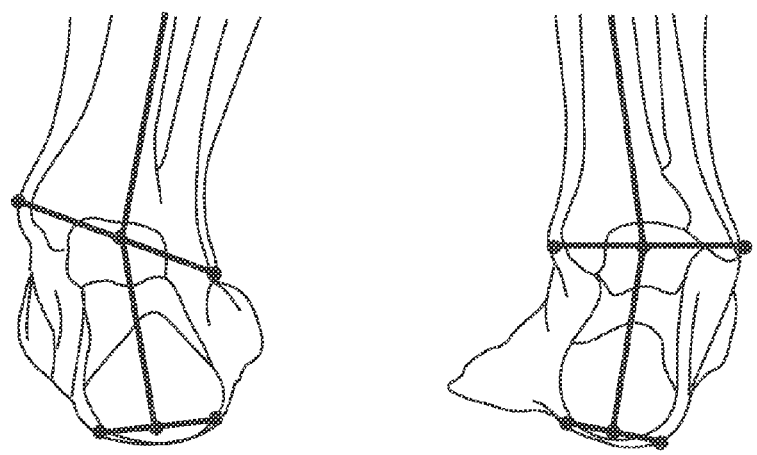
FIG. 12 shows the heel and ankle bones of a human.

From the camera and pressure plate results relationships are determined between recognisable features of the pressures curves shown in the display screens (e.g. maxima or minima, swings from pronation to supination or vice versa) and movements, e.g. rotations, of the bones in the kinematic chain attached to the foot or of the foot itself. Both normal and abnormal motions may be characterised in this way. For example a relationship between heel or rearfoot pronation and tibia internal rotation and a relationship between rearfoot or heel supination and tibia external rotation can be determined as shown schematically in FIG. 12. This relationship is caused by the need to maintain balance so that heel pronation is associated with tibia internal rotation so that the person does not fall sideways. Another example of a relationship is the appearance of pressure peaks in the midfoot balance curve indicating pronation at about 20 to 40% of the time between- .heel impact and toe liftoff which is caused by naviculare dropdown.

These relationships are recorded and stored in memory as specific features in the curves of any of heel pronation/supination, midfoot pronation/supination, forefoot pronation/supination, forefoot medial balance, and forefoot metatarsal loading or any combination of these. These special features are related to respective movements of the bones in the kinematic chain, e.g. specific rotations. The respective movements of the bones may be stored in qualitative form, i.e. if a certain pronation pressure peak appears at a certain point in one of the displays this is recorded as causing a certain rotation of one of the bones of the kinematic chain in a certain direction. Alternatively, the respective movements may be related in a quantitative way to the respective features in the display screens, i.e. the degree of pronation is related quantitatively to the angle of rotation of a bone in the kinematic chain.

Figure 5:
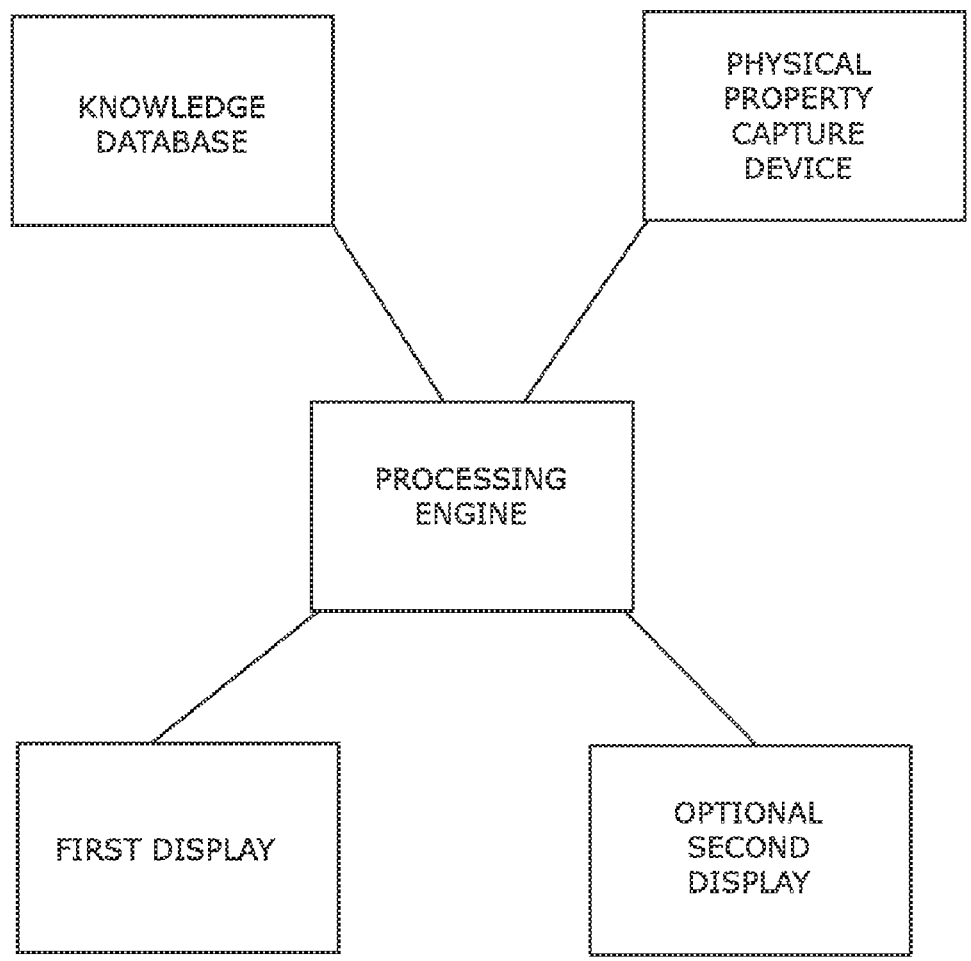
FIG. 5 shows schematically a system for diagnosing in accordance with an embodiment of the present invention.

FIG. 5 is a schematic representation of a measurement and diagnosis system 1 in accordance with an embodiment of the present invention which is simple to operate, does not require cameras except for the initial value capture with candidates and provides easily understood graphical representations of movements of the kinematic chain attached to the foot. The apparatus is for use with a new subject (after the initial subjects have been used to obtain the basic relationships) and no cameras or markers attached to the lower limb are required.

The system comprises a knowledge database 2 in which the relationships mentioned above are stored, a processing engine 3, e.g. a computer or workstation, a display 5, e.g. a conventional visual display unit, and a physical property capture device 4. Optionally, a second display 6 may be provided so that the pressure/time curves may be displayed separately from the graphical representations of the bone movements. The knowledge database includes not only the relationships described above but also 3D graphic representations of a part of the skeleton, e.g. 3D representations of the lower limb including the bones of the foot and the kinematic chain of bones attached to the foot up to the knee or up to the hip. Optionally, these 3D representations are in the form that they can be animated. The 3D representations are 20 preferably displayed using suitable 3D graphics software which allows the 3D images to be manipulated, e.g. viewed from the front or back, from either side or from above or below as well as to view the animation or to pause it. The animation may be in the form of a sequence of still images. Methods of animation of 3D graphics representations are well known to the graphics software engineer. It is not expected that the selection of particular methods of animation have a material effect on the present invention. The animations can be based on relationships recorded and stored in memory as specific features in the curves of any of heel pronation/supination, midfoot pronation/supination, forefoot pronation/supination, forefoot medial balance, and forefoot metatarsal loading or any combination of these. These special features are related to respective movements of the bones in the kinematic chain, e.g. specific rotations. The respective movements of the bones may be stored in qualitative form, i.e. if a certain pronation pressure peak appears at a certain point in one of the displays this is recorded as causing a certain rotation of one of the bones of the kinematic chain in a certain direction. Alternatively, the respective movements may be related in a quantitative way to the respective features in the display screens, i.e. the degree of pronation is related quantitatively to the angle of rotation of a bone in the kinematic chain.

The processing engine includes a processor and memory and has computer programs stored thereon for carrying out the methods of the present invention, in particular for animation of the graphic representations of the lower limb in dependence upon features derivable from the pressure measurements. The physical capture device is any suitable pressure sensing device, e.g. as supplied by RsScan, Belgium, such as type FootScan which outputs data relating to the pressure exerted by the foot or feet of the subject. FootScan as supplied by RsScan, Belgium. However, the present invention is not limited to a static pressure plate. The pressure exerted by a body part such as a foot can be measured by pressure sensors, e.g. an array of pressure sensors which are placed in or integrated into the sole of a shoe. Using such a pressure sensor, the subject may stand, hop, jump, walk or run on a flat surface or on a moving band as disclosed in WO 95/31933. Preferably the pressure sensing device is the same device or an equivalent device to the one used to generate the information on normal and/or abnormal gait previously stored in the knowledge database.

Each subject stands, hops, jumps, walks or runs on the physical capture device and the outputs in terms of pressure distributions and centres of pressure are stored. Particularly, when sportspersons train hard using repetitive similar movements, these movements may result in strain, inflammation and injury. Remedial methods are included within the scope of the present invention based on the results of the display of the time evolution of pressures. To alleviate these effects any of the following may be done: correct training errors, correct muscle imbalance, identify and correct structural abnormalities, correct running style, use designed running shoes, identify injury early, treat the injury early, prescribe and use orthotics, etc. To assist in the analysis, a software program running on the processing engine preferably converts the pressure measurements for the impacting surface of the foot into the segmented pressure zones 12-18 as described above. A or the software program running on the processing engine then prepares the displays, e.g. one or more of the displays shown in FIG. 4. These displays are the important displays of the present invention. They can be interpreted by a skilled person for diagnosis and/or a software program can assist in this interpretation. For example and optionally, a or the software program running on the processing engine detects characteristic features in the measured pressure values for the heel, midfoot and/or forefoot and in particular in the measured pressure versus time values for heel pronation/supination, midfoot pronation/supination, forefoot pronation/supination, forefoot medial balance, and/or forefoot metatarsal loading. This detection is done automatically and without the aid of cameras. Once the special characteristics of the pressure values have been determined these are translated into bone movements in accordance with the predetermined qualitative or quantitative relationships stored in the knowledge database.

These bone movements are used to animate the 3D graphics representation of the skeleton stored in the knowledge database. Some examples will now be described. As indicated above the results from the pressure measurements are obtained for 3 parts of the stance during running or walking:
rearfoot (pressure dominated by heel medial, heel lateral pressure zones)
midfoot (pressure zones from the heel and the forefoot are active)
forefoot (pressure dominated by metatarsals I, II, III, IV, V, pressure zones)

Figure 6:
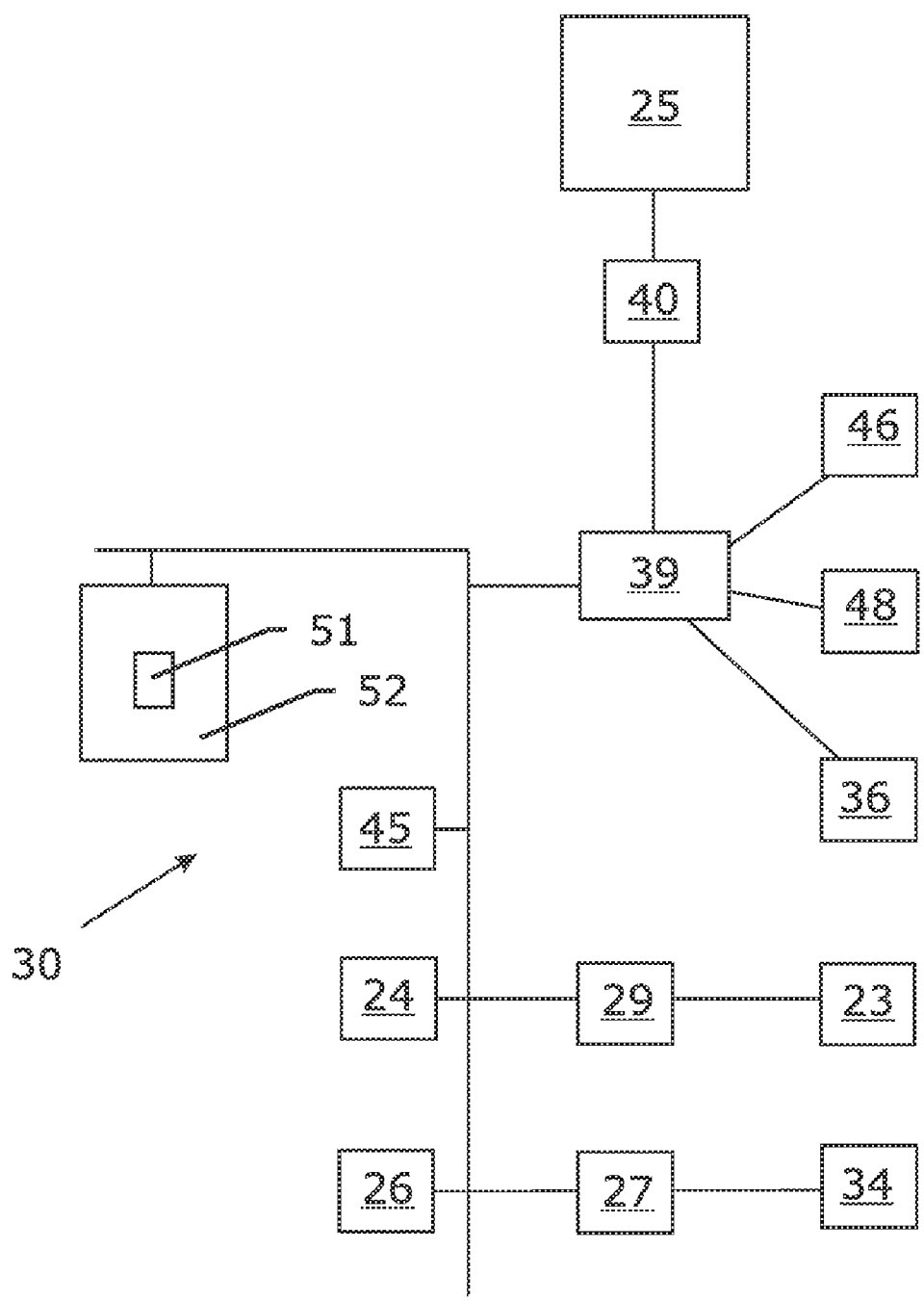
FIG. 6 shows schematically a computer system for diagnosing in accordance with an embodiment of the present invention.

FIG. 6 is a schematic representation of a computing system which can be utilized with the methods and in a system according to the present invention. A computer 30 is depicted which may include a video display terminal 34, a data input means such as a keyboard 46, and a graphic user interface indicating means such as a mouse 48. Computer 30 may be implemented as a general purpose computer, e.g. a Personal Computer or UNIX workstation.

Computer 30 includes a Central Processing Unit ("CPU") 45, such as a conventional microprocessor of which a Pentium IV processor supplied by Intel Corp. USA is only an example, and a number of other units interconnected via system bus 22. The computer 30 includes at least one memory. Memory may include any of a variety of data storage devices known to the skilled person such as random-access memory ("RAM"), read-only memory ("ROM"), non-volatile read/write memory such as a hard disc as known to the skilled person. For example, computer 10 may further include random-access memory ("RAM") 24, read-only memory ("ROM") 26, as well as an optional display adapter 27 for connecting system bus 22 to an optional video display terminal 34, and an optional input/output (I/O) adapter 29 for connecting peripheral devices (e.g., disk and tape drives 23) to system bus 22. Video display terminal 34 can be the visual output of computer 30, which can be any suitable display device such as a CRT-based video display well-known in the art of computer hardware. However, with a portable or notebook-based computer, video display terminal 34 can be replaced with a LCD-based or a gas plasma-based flat-panel display. Computer 30 further includes user interface adapter 39 for connecting a keyboard 46, mouse 48, optional speaker 36, as well as allowing optional physical value inputs from one or more physical value capture devices such as sensors 40 of an external measuring system 25. The sensors 40 may be any suitable sensors for capturing physical parameters of a person's body or limbs, e.g. feet or gait, e.g. pressure sensors of a pressure sensor array and system 25 may include a pressure plate. The pressure measurements can be displayed in the form of pressure/time plots as will be described later. These sensors may include any sensor for capturing relevant physical values required for diagnosis or remediation of injury. Additional or alternative sensors 40 for capturing physical parameters of an individual may also connected to bus 22 via a communication adapter connecting computer 30 to a data network such as the Internet, an Intranet a Local or Wide Area network (LAN or WAN) or a CAN. This allows transmission of physical values or a representation of the physical values over a telecommunications network, e.g. entering a description of an individual's pressure data at a near location, e.g. a doctor's surgery and transmitting it to a remote location, e.g. via the Internet, where a processor carries out a method in accordance with the present invention and returns 3D visualisations to a near location, i.e. for display on a visual display unit in the doctor's surgery.

The terms "physical value capture device" or "sensor" includes devices which provide values of pressures and/or force exerted by a part of the body of an animal or human, e.g. the foot. The present invention also includes within its scope that the relevant physical values read off from printed charts and are input directly into the computer using the keyboard 36 or from storage devices such as 23.

Computer 30 also includes a graphical user interface that resides within machine-readable media to direct the operation of computer 30. Any suitable machine-readable media may retain the graphical user interface, such as a random access memory (RAM) 24, a read-only memory (ROM) 26, a magnetic diskette, magnetic tape, or optical disk (the last three being located in disk and tape drives 23). Any suitable operating system and associated graphical user interface (e.g. Microsoft Windows) may direct CPU 45. In addition, computer 30 includes a control program 51 which resides within computer memory storage 52 or on other memory storage devices such as a hard disk. Control program 51 resident on storage 52 contains instructions that when executed on CPU 45 carry out the operations described with respect to any of the methods of the present invention.

In particular a knowledge database storing linked data structures may be stored on computer 30. The linked data structures record associations relating to a plurality of specific characteristics of the pressure plots and movements of the bones of the foot or bones attached to the foot. Each association is between measured characteristics of one or more of the pressure plots and the movement of the bone in question. The associations may also be stored as analytical equations relating, for example, a degree of supination/pronation to the movement of a bone.

In the example depicted in FIG. 6, the computer program product (i.e. control program 51) can reside in computer storage. However, it is important that those skilled in the art will appreciate that the mechanisms of the present invention are capable of being distributed as a program product in a variety of forms, and that the present invention applies equally regardless of the particular type of signal bearing media used to actually carry out the distribution. Examples of computer readable signal bearing media include: recordable type media such as floppy disks and CD ROMs and transmission type media such as digital and analogue communication links.

The apparatus according to the present invention provides plots of the pressure during time, especially the centres of pressure during time for the above three segments of the foot and/or a 3D graphical animation of the bone structure of the lower limb which is animated in accordance with movements derived from analysis of the pressure plots. This apparatus is used to measure a new subject but no camera or markers on the lower limb are required. Pressure information relating to foot motion can be displayed in Balance Screens. Preferably there are 5 graphs or pressure plots which can be visualised by the apparatus, each separately or in combination:

Heel rotation: shown in terms of supination/pronation of the rearfoot
Foot balance: shown in terms of supination/pronation of the midfoot
Forefoot Balance: shown in terms of supination/pronation forefoot
Medial forefoot Balance: flexible/rigid first ray
Metatarsal Loading A sixth screen showing forefont rotation can also be calculated and displayed.

Figure 7:
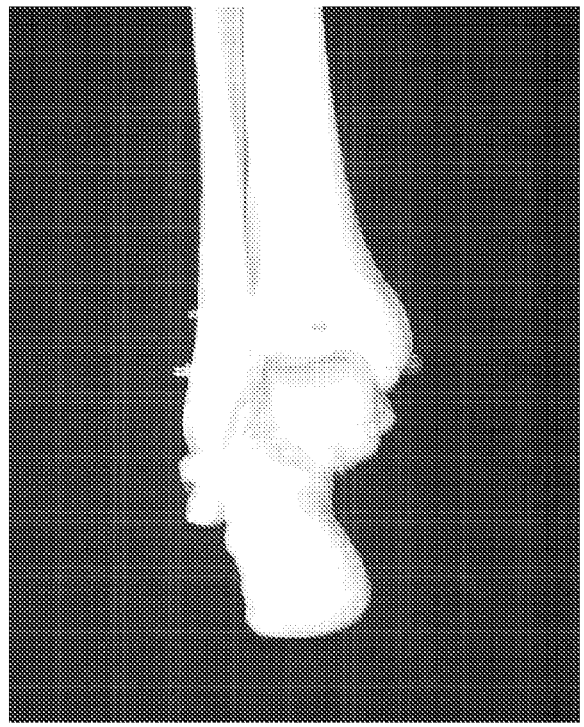
FIGS. 7 to 10 show 3D images generated in accordance with an embodiment of the present invention showing heel pronation and supination based on pressure measurements of the type shown in FIG. 11 (optionally animated).
Figure 8:
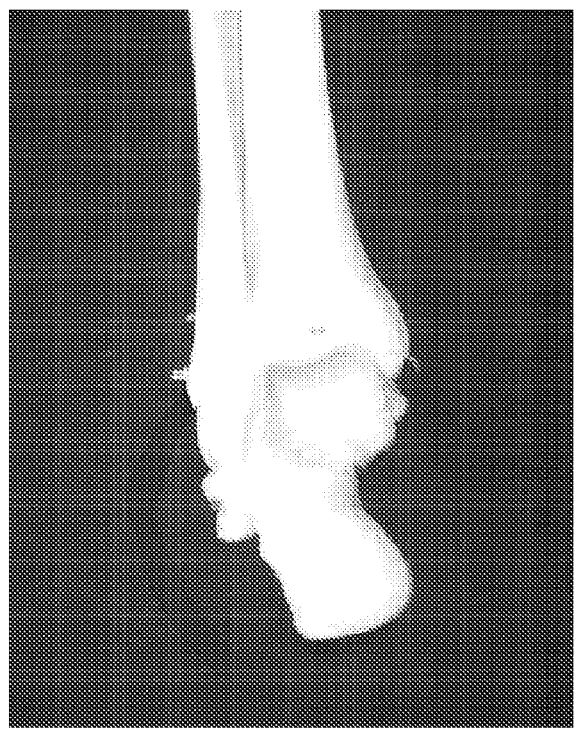
Figure 9:
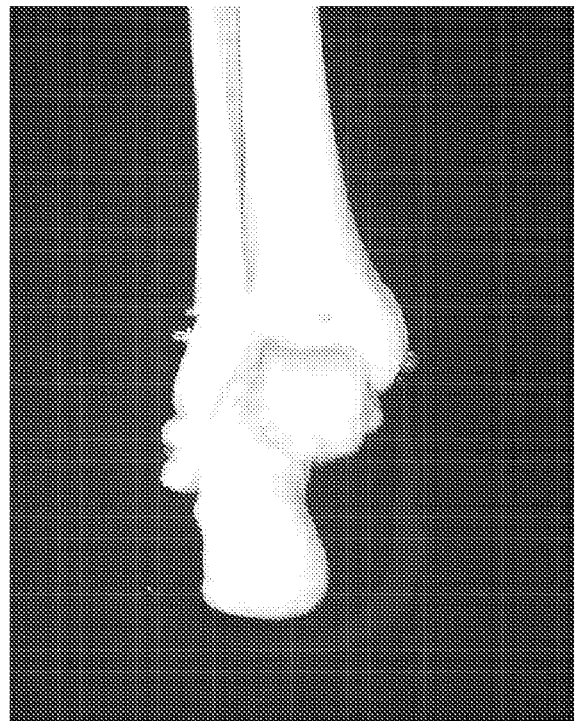
Figure 10:
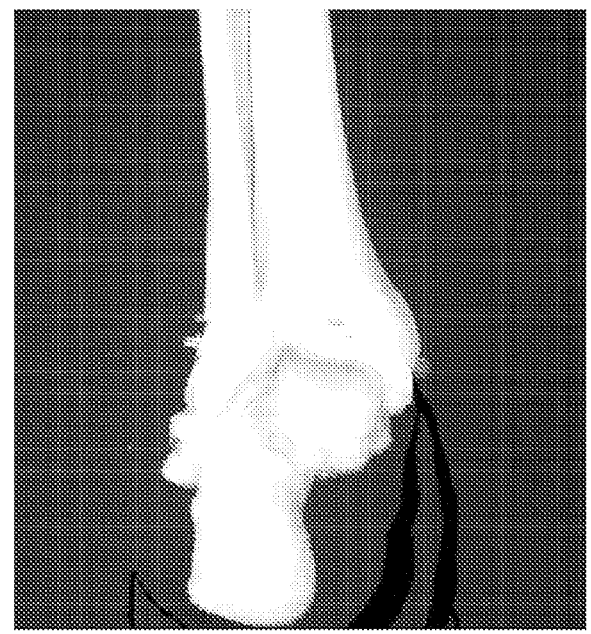
Figure 11:
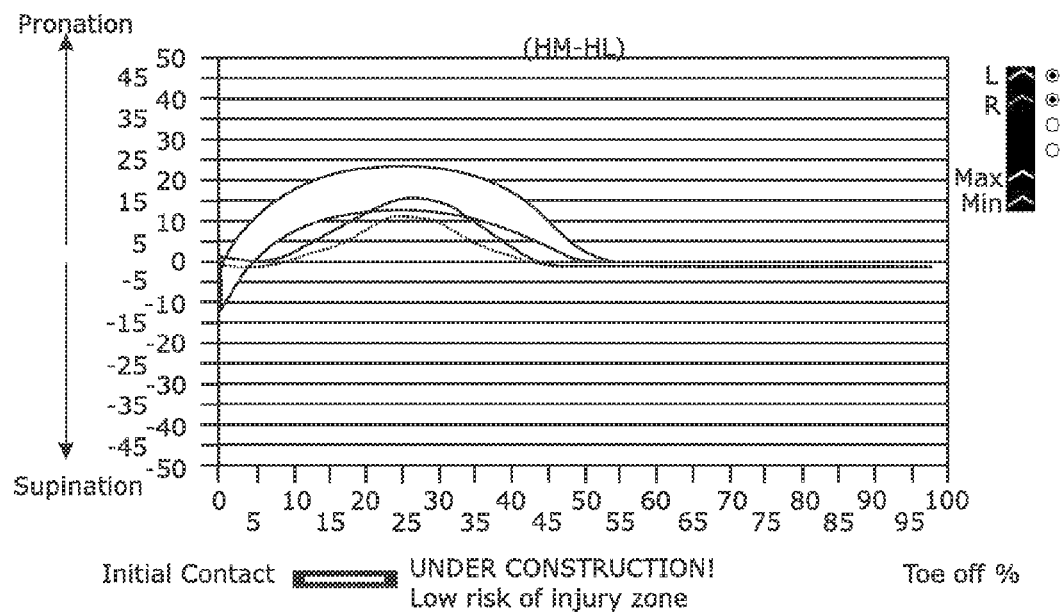
FIG. 11 shows one of the screens in accordance with an embodiment of the present invention representing the time evolution of pressures relating to heel rotation.

Examples of the 3D display of heel rotation are shown in FIGS. 7 to 10. The rearfoot is visualised from the back FIG. 7 shows the situation when the left foot is in a neutral position as determined by analysis of the pressure plots. FIG. 8 shows supination, and FIGS. 9 and 10 show 5%, and 10% pronation. It is important for kinematics that not only motion of the calcaneus but also of the subtalar joint is rendered correctly in the 3D representations in accordance with the present invention. Correlations are generated in accordance with the present invention between rearfoot pronation and tibia internal rotation, and rearfoot supination and tibia external rotation. These rotational motions are also displayed correctly in the animations. FIG. 11 shows a screen plot of the heel rotation, i.e. the temporal variation of the heel pressures represented as the medial heel pressure minus the lateral heel pressure: HM−HL. The 3D representations shown in FIGS. 7 to 10 are derived from interpreting this type of plot.

Figure 13:
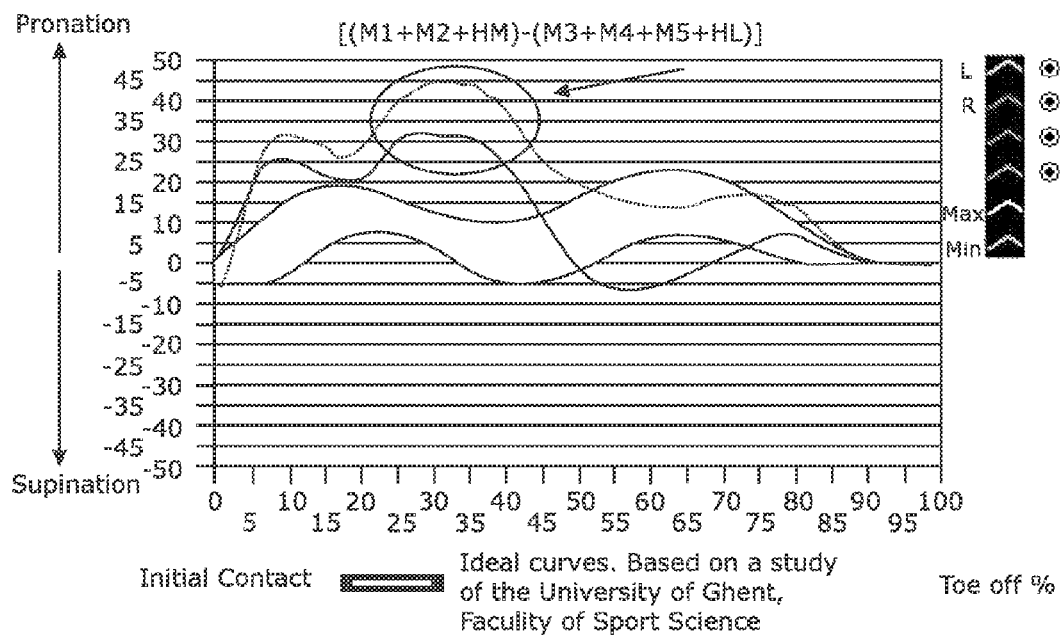
FIGS. 13 and 14 show one of the screens in accordance with an embodiment of the present invention representing the time evolution of pressures relating to foot balance.
Figure 14:
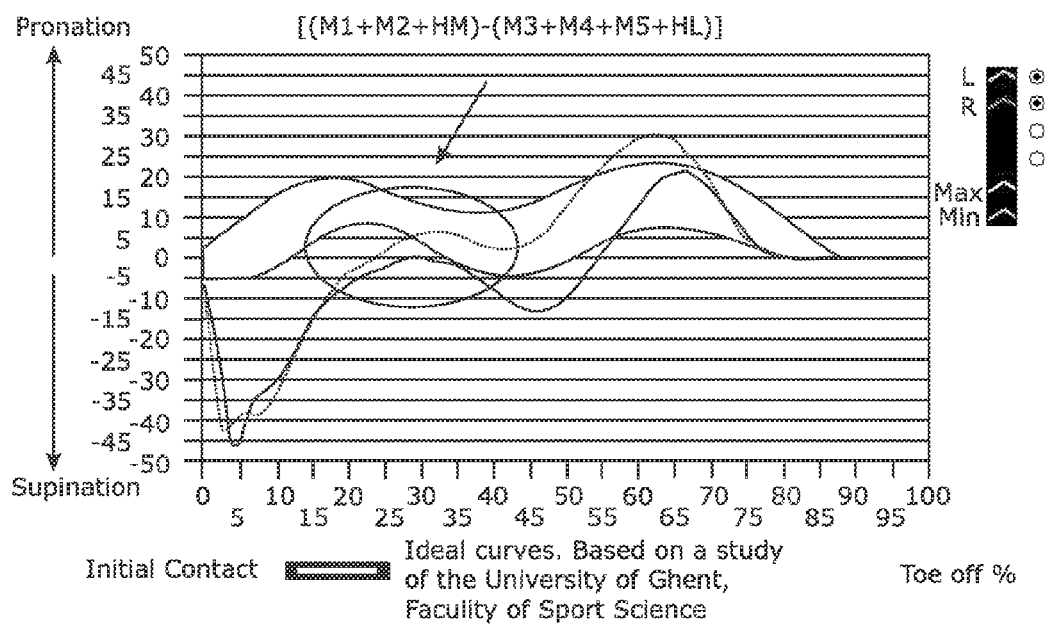

The foot balance screen is shown in FIGS. 13 and 14 in which the time evolution of pressure on the midfoot is displayed for two different subjects, respectively. The Y axis of the plot is the degree of pronation or supination and the X axis is time, e.g. the percentage of the time between heel impact and toe lift-off. On this display values obtained for a normal average of the population is shown in white as a reference (as in all such screens of this type described in relation to this invention). The two traces give the trajectories of the centres of pressure as a function of time for the left and right foot. The traces are calculated in an embodiment of the present invention by:

$$(M-HL)+(M1+M2-M3-M4-M5)=(HM+M1+M2)-(HL+M3+M4+M5)$$

In this equation HM is the medial heal pressure from zone 12, HL the lateral heel pressure from zone 13, M1-M5 are the pressure values for the pressures zones 14-18 from the metatarsal bones. One can see from the left hand side of the above equation that the pressure difference between the two sides of the foot is being calculated. A large pressure value indicates a large amount of pronation or supination. A change of maximum pressure from supination to pronation means a rolling of the foot. All such changes are related to bone positions, e.g. of the tibia and can be translated to bone movements in the kinematic chain of and from the foot. A skilled person can interpret these plots and make a suitable diagnosis. The present invention also includes further software tools to assist in the diagnosis.

Figure 15:
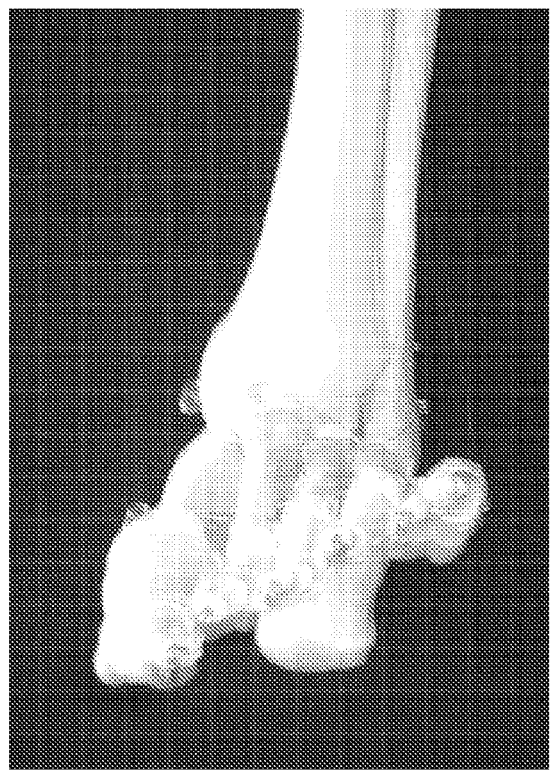
FIGS. 15 and 16 show 3D images generated in accordance with an embodiment of the present invention from pressure measurements as shown in FIGS. 13 and 14 showing foot balance (optionally animated).
Figure 16:
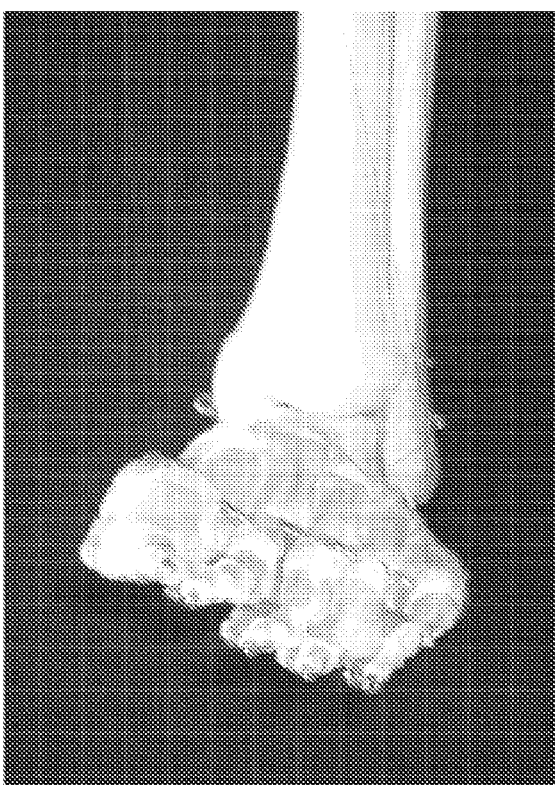

For example, in an optional embodiment of the present invention, maximum values of pronation and supination in these plots and/or changes between prontation and supination are detected by a software algorithm and are converted into a 3D animation of the bone structure. These bone movements related to foot balance are then displayed correctly in the 3D animation (optionally animated)—as shown in FIGS. 15 and 16, this time viewed from the front. FIG. 15 shows midfoot pronation and FIG. 16 shows midfoot supination.

Figure 17:
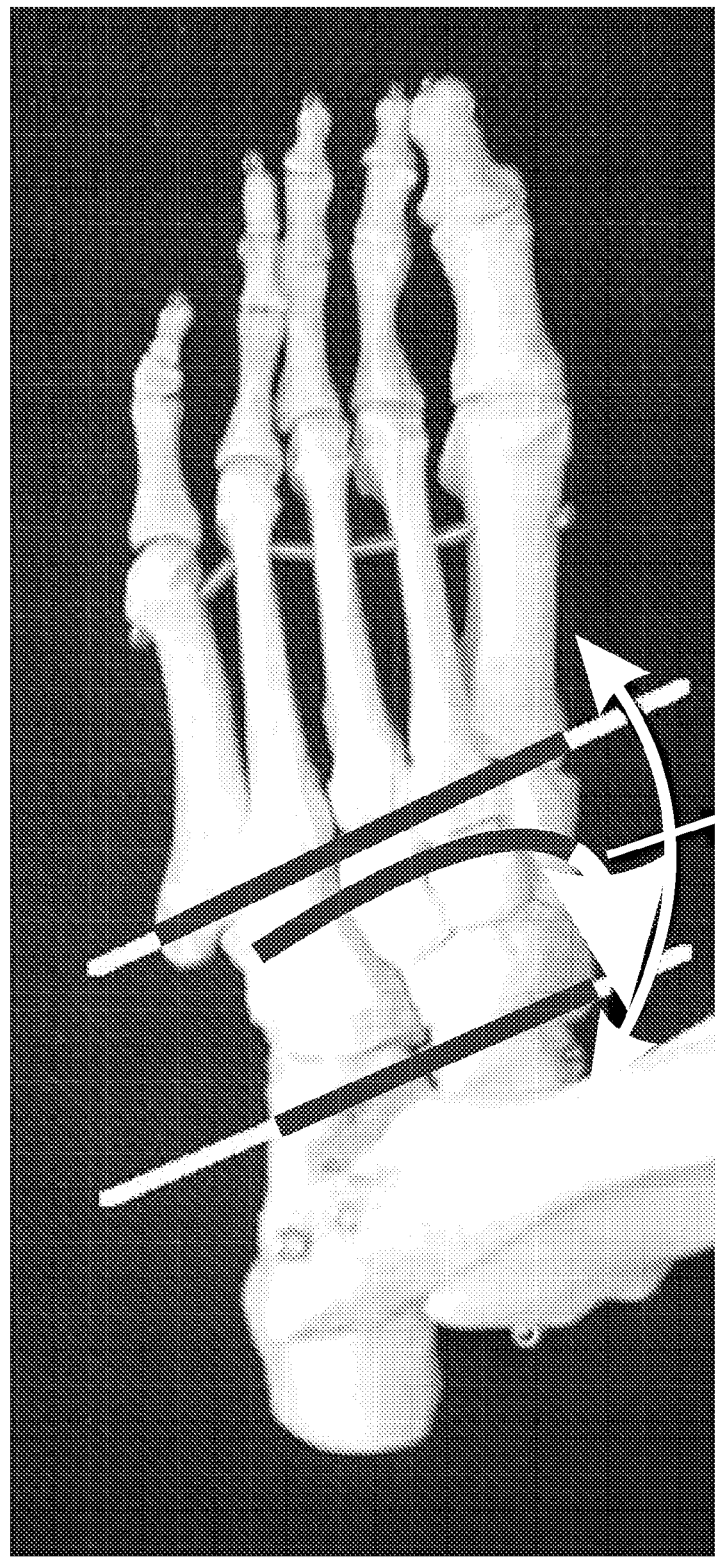
FIG. 17 shows a 3D image generated in accordance with an embodiment of the present invention showing naviculare dropdown based on pressure measurements as shown in FIGS. 13 and 14 showing foot balance (optionally animated).

A characteristic which is determined by the algorithm is a peak that can appear at midstance, e.g. between 20% and 40% of total stance time. This peak can be at any value of supination and pronation because it depends on heel and forefoot. More important is that the algorithm determines if there is a peak or not at this position. This peak can be seen in both FIGS. 13 and 14 and is marked with an arrow. The trace in FIGS. 13 and 14 obviously differs significantly from the reference range for normal subjects which is shown as the white area. This peak at the midstance position is because of naviculare dropdown on the medial side. This is displayed correctly in the 3D animation as shown in FIG. 17, this time from above.

Figure 20:
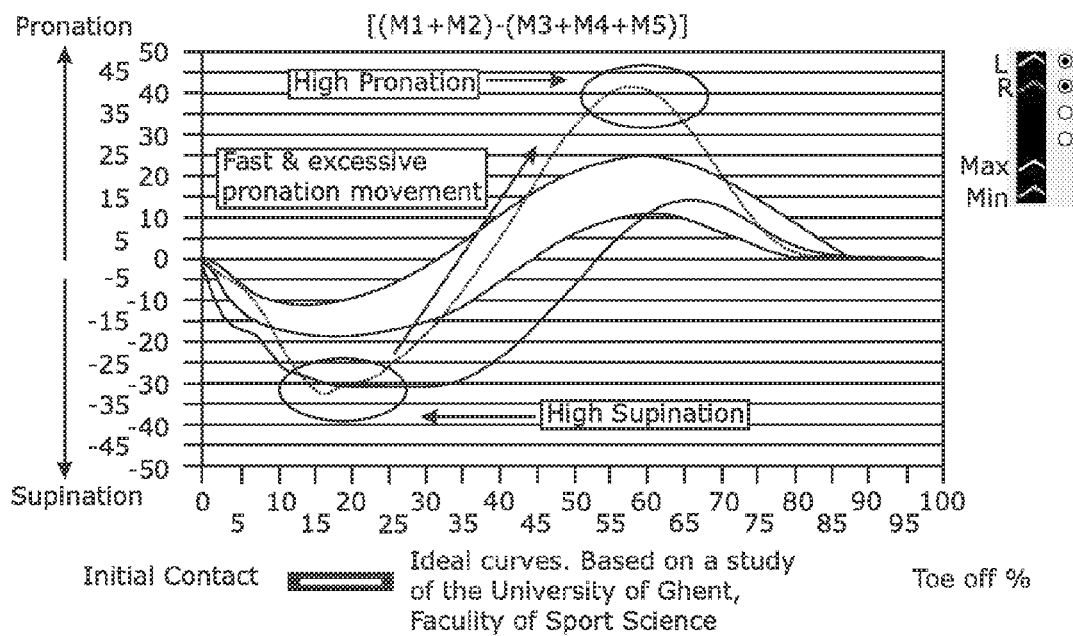
FIG. 20 shows one of the screens in accordance with an embodiment of the present invention representing the time evolution of pressure relating to forefoot balance.

A screen showing Forefoot Balance displays forefoot pronation/supination (FIG. 20). The reference curves determined for normal averages of the population are shown in white. When the curve stays within the ranges shown by the white zone there is a normal pronation movement.

Figure 18:
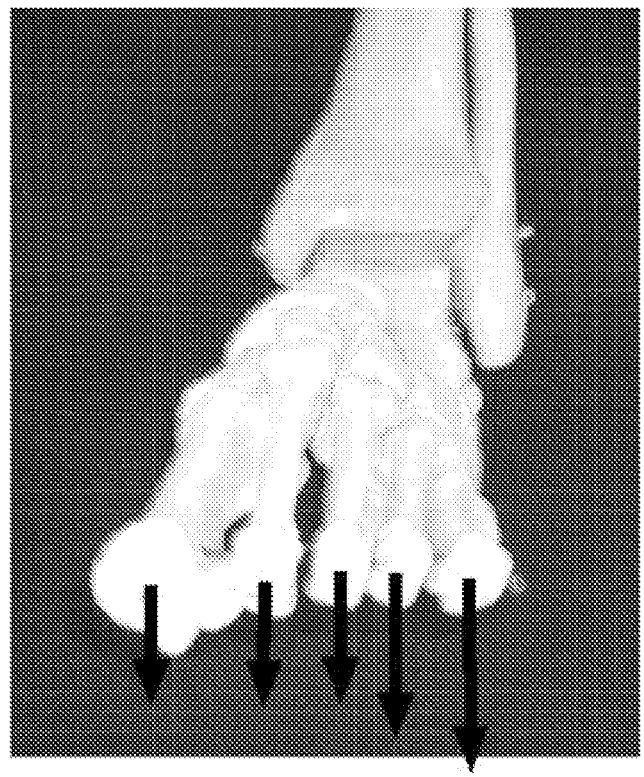
FIGS. 18 and 19 show 3D images generated in accordance with an embodiment of the present invention from pressure measurements as shown in FIG. 20 showing forefoot balance (optionally animated).
Figure 19:
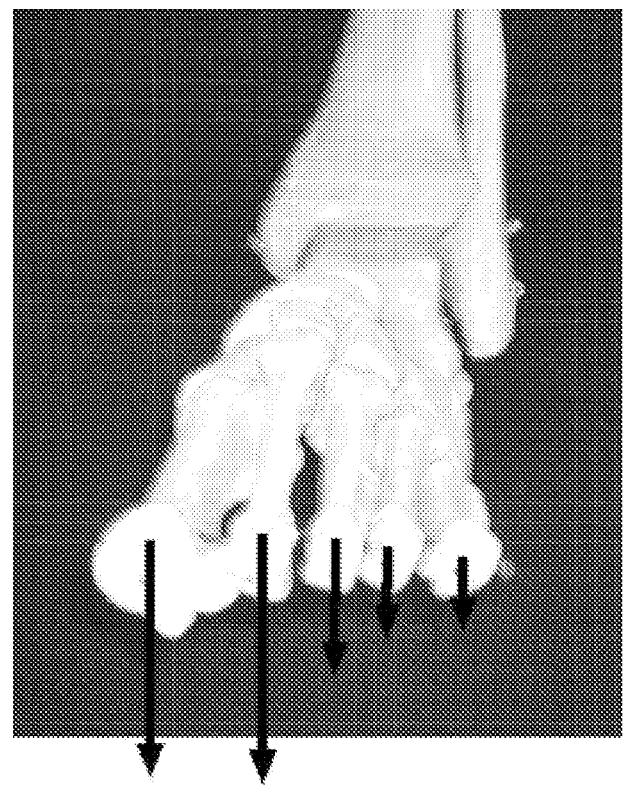

The forefoot balance is calculated in one embodiment of the present invention as: (M1+M2)−(M3+M4+M5). This equation compares the pressures on each side of the forefoot alone. Particularly in the lift off zone this provides an indication of how the foot has rolled to one side, e.g. the degree of supination or pronation. This can be related to bone position and movement in the kinematic chain of the foot and leg. Where forefoot pronation or supination is determined from this pressure plot, it is displayed in the 3D animation—see FIGS. 18, 19. As the metatarsal bones are completely on the ground no deflections or movements can be seen. In this case a visual indication of the pressure can be displayed on the 3D animation, e.g. by means of arrows whose length is related to the pressure as shown in FIGS. 18, 19. FIG. 18 shows forefoot supination and FIG. 19 shows forefoot pronation.

FIG. 20 shows a rapid change from supination to pronation in the midstance region which is visualised on the 3D animation as shown in FIGS. 18 and 19 by the change in length of the arrows in a short time. It indicates that the subject rolls the foot as the weight distribution changes from behind to in front of the heel.

Figure 21:
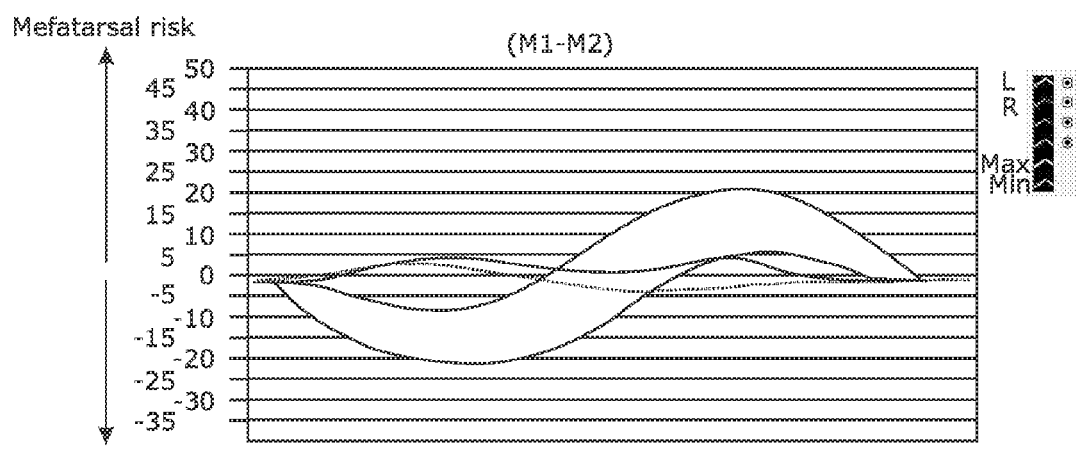
FIG. 21 shows one of the screens in accordance with an embodiment of the present invention representing the time evolution of pressures relating to medial forefoot balance.
Figure 22:
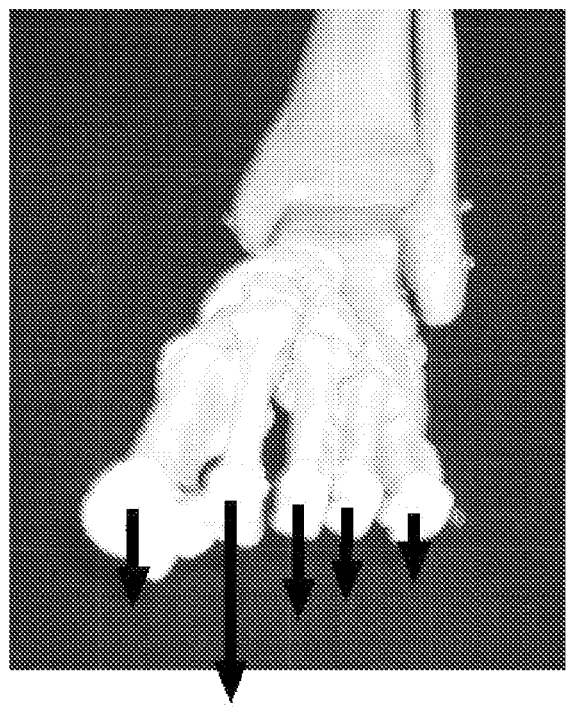
FIG. 22 shows a 3D image generated in accordance with an embodiment of the present invention from pressure measurements as shown in FIG. 21 showing medial forefoot balance (optionally animated).

A further screen is the Forefoot Medial Balance. This plots a comparison between the pressure under metatarsal II and that under I. For instance a plot of the difference in pressure between metatarsal II and I can be displayed. If this value is greater that 0, then the pressure under II is greater than under I and there is a flexible first ray—see FIG. 21 and the corresponding 3D representation (optionally animated) in FIG. 22. If the value is less than 1 then the pressure under II is less than under I and there is a rigid first ray. This display is calculated by: M2−M1

Figure 23:
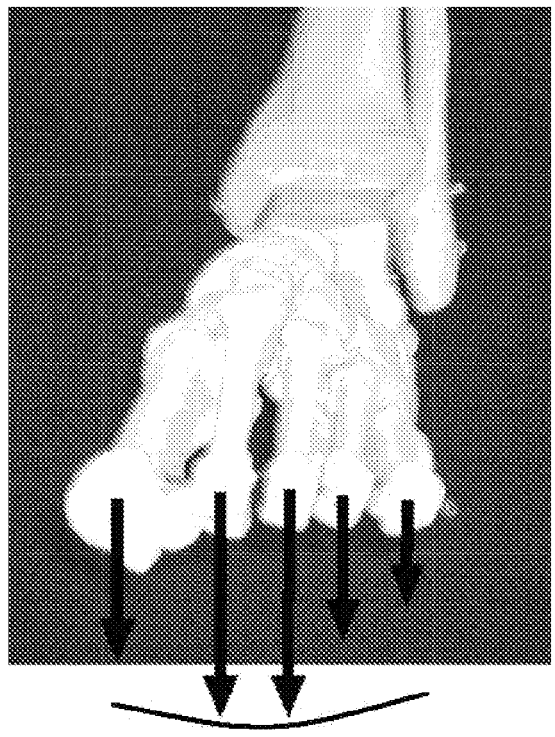
FIG. 23 shows a 3D image generated in accordance with an embodiment of the present invention from pressure measurements as shown in FIG. 24 showing metatarsal loading (optionally animated).
Figure 24:
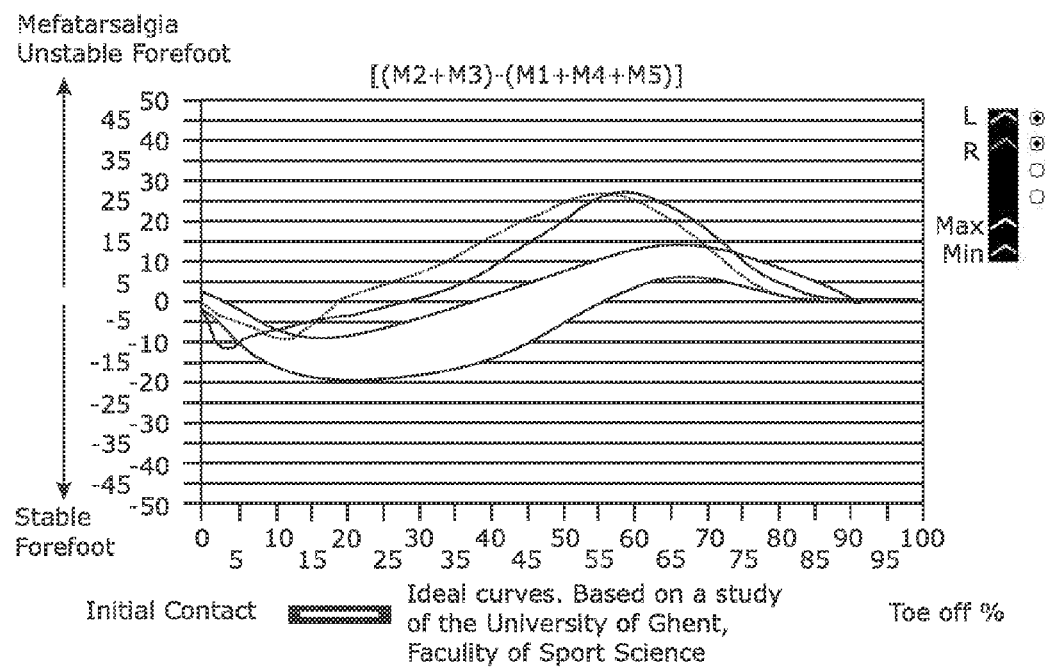
FIG. 24 show one of the screens in accordance with an embodiment of the present invention representing the time evolution of pressures relating to metatarsal loading.
Figure 25:
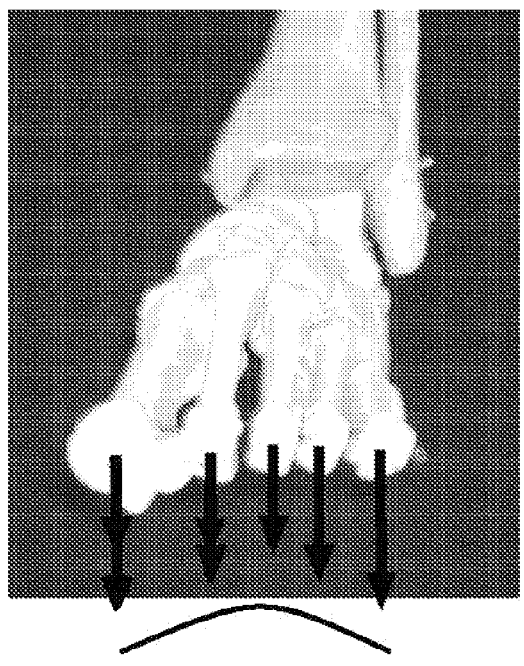
FIGS. 25 shows a 3D image generated in accordance with an embodiment of the present invention from pressure measurements as shown in FIG. 26 showing metatarsal loading (optionally animated).
Figure 26:
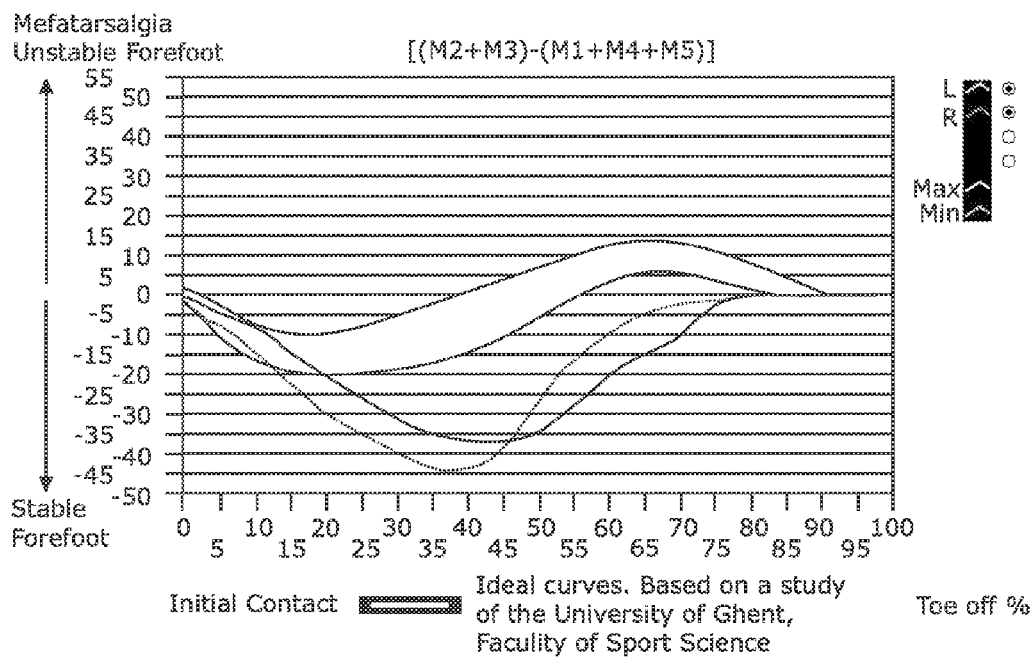
FIG. 26 shows one of the screens in accordance with an embodiment of the present invention representing the time evolution of pressures relating to metatarsal loading.

A further screen which is useful is the Metatarsal loading. A plot is displayed which compares the time evolution of pressures applied by the outer metatarsals with those applied by the inner ones. For example the pressures under II and m may be added and the sum subtracted from the sum of I, IV and V metatarsals: (M1+M3)−(M1+M4+M5). If the calculated value is greater than zero then the pressure under II and III is greater than under I and IV and V. This indicates an unstable forefoot as is displayed in 3D in FIG. 23 and the pressure plot is shown in FIG. 24. If the calculated value is less than zero then the pressure under II and III is less than under I and IV and V indicative of a stable foot. The 3D representation of this situation is shown in FIG. 25 and the pressure plot in FIG. 26. The stable forefoot has a pressure distribution more like that of an arch which is a more stable configuration.

Figure 27A:
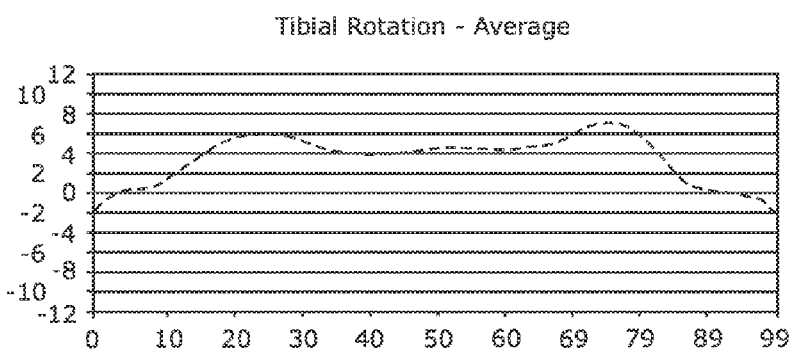
FIGS. 27 and 28 show correlations between pressure measurements according to the present invention and bone movements measurements on individuals.
Figure 27B:
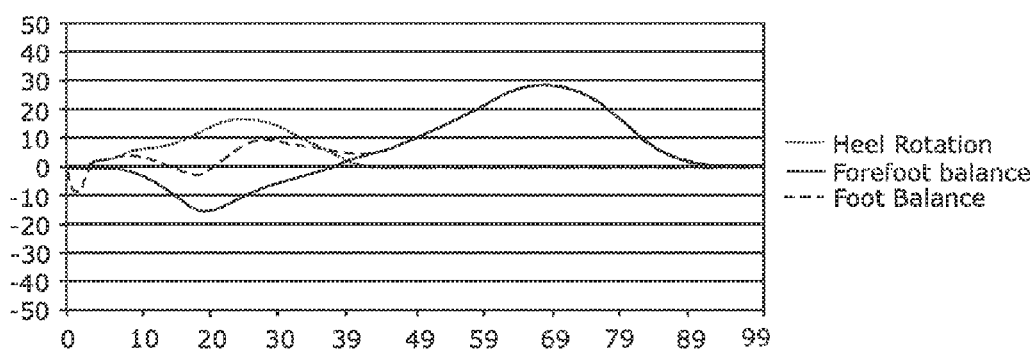

The relationship between the pressure measurements mentioned above and the bone movements is shown schematically in FIGS. 27 and 28. In FIG. 27*a* the tibial rotation is shown. In FIG. 27*b* pressure plots of heel rotation forefoot balance and foot balance are shown for the same subject. By analysis of these pressure plots a significant correlation with the bone movements is obtained. As can be see from FIG. 27*b* the peak on the right in the foot balance curve correlates with the peak in the tibia rotation on the right in FIG. 27*a*. Similarly, the peak on the left in the heel rotation in FIG. 27*b* correlates with the peak on the let in the tibia rotation.

Figure 28A:
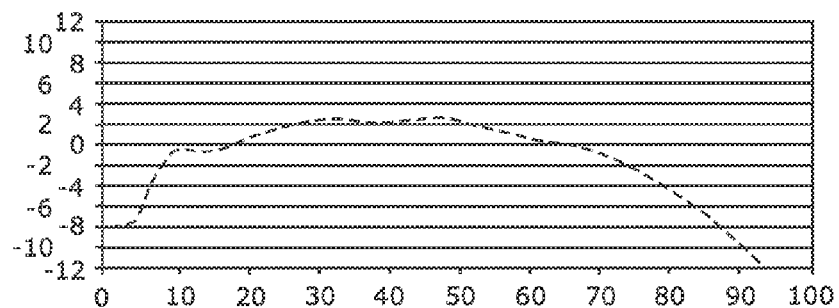
Figure 28B:
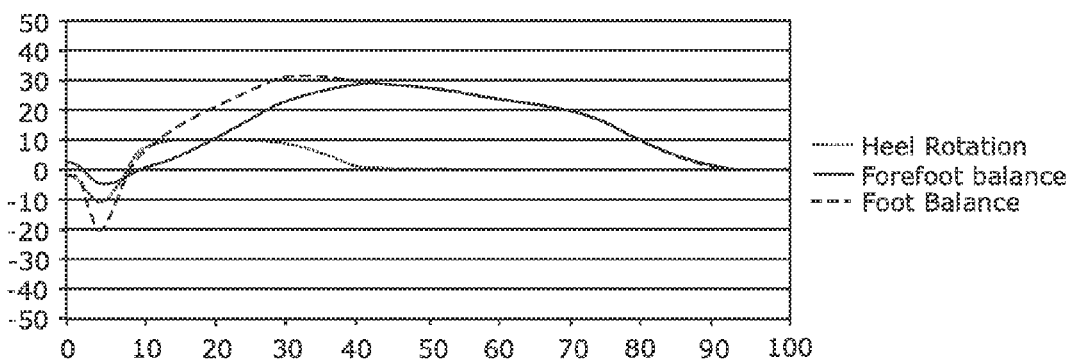

In FIG. 28*a* the heel eversion/inversion is shown and in FIG. 28*b* the heel rotation, forefoot rotation and foot balance curves are shown for the same subject. The heel inversion kinematics and the heel rotation correlate to 0.988 with the curves of FIG. 28*b*.

While the invention has been shown and described with reference to preferred embodiments, it will be understood by those skilled in the art that various changes or modifications in form and detail may be made without departing from the scope and spirit of this invention as defined in the attached claims. For example, in an alternative embodiment of the present invention the 3D representations are obtained by an alternative method. First of all a large number of 3D representations in the form shown in the attached figures of the lower skeleton from a large number of persons are stored in the knowledge database associated with the relevant pressure plots for each subject. For example videos may be stored indexed by a relational database and linked thereby to the pressure plots.

When a new subject is measured the computer program residing in the processing engine regresses the new data against the existing and selects an existing video which comes closest to matching the measured data. If no existing data matches the new data sufficiently the computer may report finding no match. Once a match is found this match is then displayed. The disadvantage of this method is that more measurement need to be made with subjects wearing markers and this inconvenient.

The invention claimed is:

1. A method of displaying a 3D representation of bones of the foot and bones attached thereto of a human or animal either when stationary or during motion using a pressure sensing device, the method comprising:
capturing from the pressure sensing device pressures exerted by the foot during standing or motion and deriving therefrom pressure values for segments of the impacting foot surface, wherein the segments include at least a lateral heel zone, a medial heel zone, and a zone for each metatarsal 1 to 5;
deriving absolute and relative movements of the bones of the foot and of the kinematic chain of bones attached thereto from the pressure values captured in each of the zones; and
displaying an animated 3D representation of the bones of the foot and of the kinematic chain of bones attached thereto based on the absolute and relative bone movements.

2. A method according to claim 1, further comprising the step of deriving from the captured pressure values a degree of pronation or supination of at least a heel segment including the lateral and the medial heel zone and forefoot segments including the zones for the metatarsals 1 to 5.

3. The method according to claim 2 further comprising displaying the degree of pronation or supination of each of at least the heel segment and the forefoot segment as a function of a time in separate displays.

4. The method according to claim 3, further comprising capturing from the pressure sensing device pressures on the foot when stationary or during motion and deriving therefrom a degree of pronation or supination of at least the heel and the midfoot and forefoot.

5. The method according to claim 4, further comprising displaying the degree of pronation or supination of each of at least the heel and the midfoot the forefoot as a function of a time in separate displays.

6. The method according to claim 3, further comprising displaying the degree of pronation or supination as a function of the time elapsed between contact by the heel and lift-off of the forefoot.

7. The method according to claim 3, further comprising displaying a reference degree of pronation or supination of at least the heel and the forefoot at the same time as displaying the degree of pronation or supination of at least the heel and the forefoot of the human or animal.

8. The method according to claim 7, further comprising displaying a reference degree of pronation or supination of at least the heel and the midfoot and forefoot at the same time as displaying the degree of pronation or supination of at least the heel, the midfoot and the forefoot of the human or animal.

9. A computer program product comprising code, which when executed on a processing engine, carries out the method of claim 1.

10. A non-transitory machine readable storage device storing the computer program product of claim 9.

11. An apparatus for displaying a 3D representation of bones of the foot and bones attached thereto of a human or animal either when stationary or during motion using a pressure sensing device, comprising:
means for capturing from the pressure sensing device pressures on the foot when standing or during motion and for deriving therefrom pressure values for segments of the impacting foot surface, wherein the segments include at least a lateral heel zone, a medial heel zone, and a zone for each metatarsal 1 to 5;
means for deriving absolute and relative movements of the bones of the foot and of the kinematic chain of bones attached thereto from the pressures captured in each of the zones; and
means for displaying an animated 3D representation of the bones of the foot and of the kinematic chain of bones attached thereto based on the absolute and relative bone movements.

12. An apparatus according to claim 11, further comprising means for deriving from the captured pressures a degree of pronation or supination of at least the heel including the lateral and the medial heel zones and a forefoot including the zones for the metatarsals 1 to 5.

13. The apparatus according to claim 12, further comprising means for displaying the degree of pronation or supination of each of at least the heel and the forefoot as a function of a time in separate displays.

14. The apparatus according to claim 13, further comprising means for deriving from the pressures measured by the pressure sensing device a degree of pronation or supination of at least the heel and the midfoot and forefoot and means for displaying the degree of pronation or supination of each of at least the heel and the midfoot the forefoot as a function of a time in separate displays.

15. The apparatus according to claim 12, further comprising means for displaying the degree of pronation or supination as a function of the time elapsed between contact by the heel and lift-off of the forefoot.

16. The apparatus according to claim 12, further comprising means for displaying a reference degree of pronation or supination of at least the heel and the forefoot at the same time as displaying the degree of pronation or supination of at least the heel and the forefoot of the human or animal.

17. The apparatus according to claim 16, further comprising means for displaying a reference degree of pronation or supination of at least the heel and the midfoot and forefoot at the same time as displaying the degree of pronation or supination of at least the heel, the midfoot and the forefoot of the human or animal.

* * * * *